(12) United States Patent
Parekh et al.

(10) Patent No.: US 12,298,318 B2
(45) Date of Patent: May 13, 2025

(54) TARGETING LIGANDS FOR TAU PATHOLOGY

(71) Applicant: Texas Children's Hospital, Houston, TX (US)

(72) Inventors: Parag Parekh, Houston, TX (US); Ananth Annapragada, Manvel, TX (US)

(73) Assignees: Texas Children's Hospital, Houston, TX (US); Baylor College of Medicine, Houston, TX (US)

( * ) Notice: Subject to any disclaimer, the term of this patent is extended or adjusted under 35 U.S.C. 154(b) by 10 days.

(21) Appl. No.: 18/163,000

(22) Filed: Feb. 1, 2023

(65) Prior Publication Data

US 2023/0324411 A1    Oct. 12, 2023

Related U.S. Application Data

(63) Continuation of application No. 17/739,031, filed on May 6, 2022, now Pat. No. 11,614,451, which is a continuation-in-part of application No. 16/922,762, filed on Jul. 7, 2020, now abandoned.

(60) Provisional application No. 63/287,036, filed on Dec. 7, 2021, provisional application No. 63/185,317, filed on May 6, 2021, provisional application No. 62/871,380, filed on Jul. 8, 2019.

(51) Int. Cl.
| | |
|---|---|
| *G01N 33/68* | (2006.01) |
| *A61B 5/055* | (2006.01) |
| *C12N 15/10* | (2006.01) |
| *C12N 15/11* | (2006.01) |
| *C12N 15/115* | (2010.01) |

(52) U.S. Cl.
CPC ..... *G01N 33/6896* (2013.01); *C12N 15/1048* (2013.01); *C12N 15/111* (2013.01); *C12N 15/115* (2013.01); *A61B 5/055* (2013.01); *C12N 2310/16* (2013.01); *G01N 2800/2821* (2013.01)

(58) Field of Classification Search
CPC ........... A61B 5/055; G01N 2800/2821; G01N 2800/2814; G01N 33/6896; C12N 2310/351; C12N 2310/16; C12N 15/111; C12N 15/1048
See application file for complete search history.

(56) References Cited

U.S. PATENT DOCUMENTS

| | | | |
|---|---|---|---|
| 5,593,688 A | 1/1997 | Baldeschwieler | |
| 2015/0125516 A1 | 5/2015 | Levy et al. | |
| 2016/0069889 A1 | 3/2016 | Spetzler et al. | |
| 2017/0066797 A1 | 3/2017 | Gunatilaka et al. | |
| 2019/0101529 A1 | 4/2019 | Wang et al. | |
| 2020/0261605 A1 | 8/2020 | Annapragada et al. | |
| 2021/0128755 A1 | 5/2021 | Annapragada et al. | |
| 2021/0236662 A1 | 8/2021 | Tanifum et al. | |

FOREIGN PATENT DOCUMENTS

| | | | |
|---|---|---|---|
| CN | 107106708 A | 8/2017 | |
| WO | 2009076539 | 6/2009 | |
| WO | WO-2016011049 A2 * | 1/2016 | ............ A61K 31/58 |
| WO | 2016057812 | 4/2016 | |
| WO | WO-2018201069 A1 * | 11/2018 | ......... A61K 49/0002 |

OTHER PUBLICATIONS

Hwang et al., Macromol Symp., 2007, 249-250(1), p. 109-115. (Year: 2007).*
Aso et al., Journal of Controlled Release, 2007, 122, p. 189-198. (Year: 2007).
Cai et al., Drug Discovery Today, 2018, 23(5), p. 1126-1138. (Year: 2018).
Non-Final rejection issued in U.S. Appl. No. 17/739,031 on Sep. 9, 2022.
International Search Report and Written Opinion issued in PCT app. No. PCT/US20/41045 on Dec. 3, 2020.
International Preliminary Report on Patentability issued in PCT app. No. PCT/US20/41045 on Jan. 11, 2022.
International Search Report and Written Opinion issued in Patent Cooperation Treaty No. PCT/US23/66550 on Aug. 29, 2023.
Tanifum et al., "Intravenous Delivery of Targeted Liposomes to Amyloid-beta Pathology in APP/PSEN1 Transgenic Mice," Plos One, Oct. 31, 2012 (Oct. 31, 2012), vol. 7, Iss. 10, pp. 1-14.
Parekh et al. "A surrogate marker for very early-stage tau pathology is detectable by molecular magnetic resonance imaging," Theranostics, Jul. 18, 2022 (Jul. 18, 2022), vol. 12, Iss. 12, pp. 5504-5521.

(Continued)

*Primary Examiner* — Michael G. Hartley
*Assistant Examiner* — Leah H Schlientz
(74) *Attorney, Agent, or Firm* — Kern Kendrick, LLC; Benjamen E. Kern; Charlemagne Kern

(57) ABSTRACT

Methods and compositions for detecting tau pathology are described. The compositions for detecting tau pathology comprise a targeting ligand that specifically binds to a cell surface marker of tau pathology, wherein the targeting ligand is linked to a liposome that includes an imaging agent. The compositions can be used in a method for imaging tau pathology in a subject that comprises administering to the subject an effective amount of the composition to a subject and imaging at least a portion of the subject to determine if that portion of the subject exhibits tau pathology. The compositions can also be used to detect tau pathology in biological samples obtained from a subject.

15 Claims, 22 Drawing Sheets

Specification includes a Sequence Listing.

(56) References Cited

OTHER PUBLICATIONS

S. Krishnaswamy et al.: "Antibody-derived in vivo imaging of Tau pathology", The Journal of Neuroscience, vol. 34, No. 50, Dec. 10, 2014, pp. 16835-16850, ISSN: 0270-6474, DOI: 10.1523/JNEUROSCI. 2755-14.2014.
Extended European Search Report issued in European application No. 20836078.4, mailing date Oct. 6, 2023.
Japan Patent Office, Office Action issued in Japanese Patent Application No. 2022-500781, dated Jul. 30, 2024 (3 pages).
Chinese National Intellectual Property Administration, First Office Action issued in Chinese Patent Application No. 202080062422.5, dated Aug. 2, 2024 (3 pages).
International Preliminary Report on Patentability issued in PCT/US2023/066550 on Nov. 7, 2024.

\* cited by examiner

SEQUENCE LISTING

```
Sequence total quantity: 29
SEQ ID NO: 1              moltype = DNA  length = 23
FEATURE                   Location/Qualifiers
misc_feature              1..23
                          note = Synthetic
source                    1..23
                          mol_type = other DNA
                          organism = synthetic construct
SEQUENCE: 1
gatatgtcta gagcctcaga tca                                              23

SEQ ID NO: 2              moltype = DNA  length = 21
FEATURE                   Location/Qualifiers
misc_feature              1..21
                          note = Synthetic
source                    1..21
                          mol_type = other DNA
                          organism = synthetic construct
SEQUENCE: 2
cggagttatg ttagcagtag c                                                21

SEQ ID NO: 3              moltype = DNA  length = 21
FEATURE                   Location/Qualifiers
misc_feature              1..21
                          note = Synthetic
source                    1..21
                          mol_type = other DNA
                          organism = synthetic construct
```

```
SEQUENCE: 3
cggagttatg ttagcagtag c                                         21

SEQ ID NO: 4            moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 4
cggagttatg ttagcagtag c                                         21

SEQ ID NO: 5            moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 5
cccccacgg tctccgctcc acaagttcac                                 30

SEQ ID NO: 6            moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 6
cccccacgg tctccgctcc acaagttcac                                 30

SEQ ID NO: 7            moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 7
ccccccacgg tctccgctcc acaggttcac                                30

SEQ ID NO: 8            moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 8
ccccccacgg tctccgctcc acaggttcac                                30

SEQ ID NO: 9            moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 9
ctcgtgggtg tgtggtggtg ttgttgtgtg                                30

SEQ ID NO: 10           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 10
ccccccacgg tctccgctcc acaagcccac                                30

SEQ ID NO: 11           moltype = DNA  length = 30
FEATURE                 Location/Qualifiers
misc_feature            1..30
                        note = Synthetic
source                  1..30
                        mol_type = other DNA
```

```
                        organism = synthetic construct
SEQUENCE: 11
ctcgtcccac cacaacatca tctcaacgcc                                              30

SEQ ID NO: 12           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 12
ctcgtcccac cacaacatca tctcaacgcc                                              30

SEQ ID NO: 13           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 13
ctcgtgggtg tacggtggtg ttgttgtgtg                                              30

SEQ ID NO: 14           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 14
ctccgacggg atgttcgatg agcacacact                                              30

SEQ ID NO: 15           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 15
cccccccacg gtctccgctc cacaagtcca                                              30

SEQ ID NO: 16           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 16
cccccacgg tctccgctcc acaggtccac                                               30

SEQ ID NO: 17           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 17
cccccacgg tctccgctcc acaggtccac                                               30

SEQ ID NO: 18           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 18
cccccacgg tctccgctcc acaggtccac                                               30

SEQ ID NO: 19           moltype = DNA   length = 30
FEATURE                 Location/Qualifiers
misc_feature            1..30
                        note = Synthetic
source                  1..30
```

```
                        mol_type = other DNA
                        organism = synthetic construct
SEQUENCE: 19
cccccccacg gtctccgctc cacaggttca                                          30

SEQ ID NO: 20           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 20
ctcgtcccac cacaacattg tctcaacgcc                                          30

SEQ ID NO: 21           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 21
ctcgtcccac cacaacacca tctcaacgcc                                          30

SEQ ID NO: 22           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 22
ctccgacggg gtgttcgatg agcacacact                                          30

SEQ ID NO: 23           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 23
cccccgcgg tctccgctcc acaagttcac                                           30

SEQ ID NO: 24           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 24
tgggtgtgtg gtggtgttgt tgtgtgggtg                                          30

SEQ ID NO: 25           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 25
tgggtgtgtg gtggtgttgt tgtgtgggtg                                          30

SEQ ID NO: 26           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 26
cccccccacgg tctccgctcc acaagttcgc                                         30

SEQ ID NO: 27           moltype = DNA   length = 30
FEATURE                 Location/Qualifiers
misc_feature            1..30
                        note = Synthetic
```

```
source                   1..30
                         mol_type = other DNA
                         organism = synthetic construct
SEQUENCE: 27
cccccccacg gtctccgctc cacaagctca                                      30

SEQ ID NO: 28            moltype = DNA  length = 21
FEATURE                  Location/Qualifiers
misc_feature             1..21
                         note = Synthetic
source                   1..21
                         mol_type = other DNA
                         organism = synthetic construct
SEQUENCE: 28
cgctcgatag atcgagcttc g                                               21

SEQ ID NO: 29            moltype = DNA  length = 23
FEATURE                  Location/Qualifiers
misc_feature             1..23
                         note = Synthetic
source                   1..23
                         mol_type = other DNA
                         organism = synthetic construct
SEQUENCE: 29
gtcgatcacg ctctagagca ctg                                             23
```

TARGETING LIGANDS FOR TAU PATHOLOGY

CROSS-REFERENCE TO RELATED APPLICATIONS

This application is a continuation of U.S. patent application Ser. No. 17/739,031, filed on May 6, 2022, and is now issued as U.S. Pat. No. 11,614,451B2, which is a continuation in part of U.S. patent application Ser. No. 16/922,762, filed on Jul. 7, 2020, which claims the benefit of U.S. Provisional Patent Application No. 62/871,380, filed on Jul. 8, 2019. U.S. patent application Ser. No. 17/739,031 also claims the benefit of U.S. Provisional Patent Application No. 63/185,317, filed May 6, 2021, and U.S. Provisional Patent Application No. 63,287,036, filed on Dec. 7, 2021. Each of these applications is incorporated by reference herein in its entirety.

SEQUENCE LISTING

A Sequence Listing has been submitted electronically in XML format and is hereby incorporated by reference in its entirety. The XML copy, created on May 4, 2023, is named Alzeca-ADx-002-USCIPW-SequenceListing_ST26.xml and is 36,743 bytes in size.

BACKGROUND

The microtubule associated protein tau, coded for by the MAPT gene, is abundant in the brain and is present in neurons, glia, and other cell types. Tau expressed in six isoforms has a vast array of post-translational modifications, including glycosylation, glycation, nitration, ubiquitination, and more than 80 potential phosphorylation sites expanding the complexity of its role in health and disease. A definitive feature of many neurodegenerative diseases, including Alzheimer's disease (AD), frontotemporal lobar degeneration (FTLD), and Parkinson's disease (PD) (collectively termed "tauopathies"), is the presence of intracellular aggregated filamentous tau.

The transition from physiological soluble tau to insoluble tau is primarily associated with changes in its phosphorylation state leading to oligomeric tau and tau fibrils known as paired helical fragments (PHF) that form characteristic neurofibrillary tangles (NFT). Tau aggregates are also capable of "infecting" a healthy cell, inducing further misfolding, aggregation, and neurotoxicity. Studies of intercellular propagation demonstrate passage through an extracellular phase that progresses throughout the brain.

The National Institute of Aging-Alzheimer's Association (NIA-AA) Research Framework identifies extracellular deposits of amyloid beta (A), presence of intraneuronal hyperphosphorylated tau (T), and markers of neurodegeneration or neuronal injury (N) as characterization of AD. Each biomarker is scored either positive or negative. To be on the AD continuum, A+ (Amyloid positive) is required, while a positive diagnosis of AD requires A+ and T+. Biomarker detection can be by: (i) positron emission tomography (PET) imaging of amyloid and tau; (ii) cerebrospinal fluid (CSF) detection of reduced $A\beta_{42}$, and/or high $A\beta_{40}/A\beta_{42}$ and high phosphorylated tau and total tau; or (iii) neuronal injury or degeneration as shown by structural brain magnetic resonance imaging (MRI). Tracking of brain pathology in longitudinal studies suggests that tau pathology may precede $A\beta$ accumulation but is undetectable based on current biomarker detection threshold levels and is amplified catastrophically by independent $A\beta$ deposition. The ATN research framework-based diagnosis of AD is therefore limited by tau pathology detection. Other factors to consider in the development of tau detection methods include the invasive nature of CSF sampling requiring lumbar puncture, and in the case of PET imaging, exposure to ionizing radiation, high cost, well documented side effects, irregular availability in primary care settings, and uneven geographical availability of PET scanners and isotopes. The short half-life of PET agents also poses challenges for the detection of intracellular tau in the early stages of tau pathology formation. Blood based markers are very promising, but only provide an indirect measure that cannot provide information on the localization of tau pathology in brain. Methods to detect early tau pathology that avoid these pitfalls are therefore highly desirable.

SUMMARY

The initiation of tau pathology is marked by abnormal phosphorylation of tau. Hyperphosphorylative conditions in neurons may result in unique surface markers, which is consistent with an altered balance of kinase-phosphatase activity resulting in elevated levels of hyperphosphorylated tau species. The utility of such a surface marker lies in the fact that an imaging agent can bind it without needing to penetrate the cell membrane, a limitation that currently hinders tau-PET agents.

Reverse phase protein array (RPPA) analysis of a cell-based model of tau hyperphosphorylation identified several proteins that were either upregulated or downregulated by the onset of a hyperphosphorylative state. Iterative Cell-SELEX process was used to identify DNA thioaptamers that specifically bind such cells. High T1 relaxivity PEGylated liposomes bearing macrocyclic Gd-chelates were modified to bear the thioaptamers on their surface, thus enabling targeting of the particles to the surface of hyperphosphorylative cells for contrast-enhanced MRI.

Thus, in one aspect, a new generation of molecular imaging probes is provided for in vivo detection of cells performing abnormal phosphorylation representing the initial stages of pTau formation, enabling a very early stage diagnosis of AD. In one aspect, a novel nanoparticle formulation that binds such abnormally phosphorylating cells, enabling in vivo visualization of the hyperphosphorylative state by MRI. The results demonstrate the potential of this novel platform to diagnose the development of future tau pathology and has implications for the very early stage diagnosis of Alzheimer's disease.

At the molecular level, binding targets of the thioaptamers were identified, such as vimentin, a normally intracellular protein that is specifically expressed on the surface of cells under hyperphosphorylative conditions, representing a possible biomarker of the pathological hyperphosphorylation found in AD. Cell-surface vimentin was found to be present at elevated levels on SH-SY5Y and ReN-VM cells in the hyperphosphorylative state showing elevated pTau levels. Such cells were also found to be specifically bound by the thioaptamers. In 2 month old P301S transgenic mice, elevated vimentin levels were found in cells of the hippocampus that also had elevated pTau levels, but non-transgenic siblings did not exhibit either elevated pTau or vimentin. To demonstrate vimentin as a specific target of the DNA thioaptamer, withaferin A, a small molecule vimentin ligand, was bound to Gd-containing liposomes. Both the thioaptamer targeted Gd-containing liposomes and the Withaferin targeted Gd-containing liposomes, when injected intravenously in P301S mice at 2 months of age, specifically produced signal enhancement on MRI in the brains of transgenic mice, but not in the brains of non-transgenic siblings. Untargeted Gd-containing liposomes did not show any signal enhancement in either group of mice. Practically 100% of the transgenic mice go on to develop frank tau pathology at 8 months of age or later. The targeted Gd-containing liposomes therefore serve as an M-MRI agent that can identify the development of future tau pathology in a pre-pathological state.

In one aspect, a composition is provided for identifying tau pathology, the composition comprising a targeting ligand that specifically binds to a cell surface marker of tau pathology, wherein the targeting ligand is linked to a liposome comprising an imaging agent, e.g., an MRI contrast enhancing agent. In some aspects, the targeting ligand comprises an aptamer or stabilized aptamer. In some aspects, the targeting ligand comprises a thioaptamer. In some aspects, the targeting ligand comprises a DNA nucleotide sequence selected from one or more of Tau_1 (SEQ ID NO: 5) (sometimes referred to hereinafter as "DONGYBM"), Tau_3 (SEQ ID NO: 6) (sometimes referred to hereinafter as "MUSQD"), Tau_9 (SEQ ID NO: 7), Tau_11 (SEQ ID NO: 8), Tau_10 (SEQ ID NO: 9), Tau_13 (SEQ ID NO: 10), Tau_8 (SEQ ID NO: 11), Tau_4 (SEQ ID NO: 12), Tau_17 (SEQ ID NO: 13), Tau_5 (SEQ ID NO: 14), Tau_21 (SEQ ID NO: 15), Tau_25 (SEQ ID NO: 16), Tau_7 (SEQ ID NO: 17), Tau_31 (SEQ ID NO: 18), Tau_42 (SEQ ID NO: 19), Tau_14 (SEQ ID NO: 20), Tau_19 (SEQ ID NO: 21), Tau_15 (SEQ ID NO: 22), Tau_56 (SEQ ID NO: 23), Tau_34 (SEQ ID NO: 24), Tau_23 (SEQ ID NO: 25), Tau_99 (SEQ ID NO: 26), and Tau_102 (SEQ ID NO: 27).

In some aspects, the cell surface marker of tau pathology comprises a cell surface marker of tau hyperphosphorylation. In some aspects, the cell surface marker of tau pathology comprises a protein selected from keratin 6A (KRT6A), keratin 6B (KRT6B), heat shock protein (HSP), and vimentin (VIM). In some aspects, the targeting ligand is determined to specifically bind to a cell surface marker of tau pathology using a systematic evolution of ligands by exponential enrichment (SELEX) method. In some aspects, the targeting ligand is linked to polyethylene glycol that is conjugated to a phospholipid that associates with the liposome. In some aspects, the liposome comprises a membrane, the membrane comprising: a first phospholipid; a sterically bulky excipient that is capable of stabilizing the liposome; a second phospholipid that is derivatized with a first polymer; a third phospholipid that is derivatized with a second polymer, the second polymer being conjugated to the targeting ligand; and an imaging agent that is encapsulated by or bound to the membrane.

In another aspect, a method is provided for imaging tau pathology in a subject, the method comprising: administering to the subject a detectably effective amount of a targeting ligand-liposome conjugate comprising a targeting ligand that specifically binds to a cell surface marker of tau pathology, wherein the targeting ligand is conjugated to a liposome comprising an imaging agent, and imaging at least a portion of the subject to determine if that portion of the subject exhibits tau pathology. In some aspects, the portion of the subject includes a portion of the subject's brain. In some aspects, the imaging indicates a level of tau pathology sufficient to diagnose the subject as having early stage AD. In some aspects, the method further comprises providing prophylaxis or treatment of AD to the subject. In some aspects, the imaging agent is an MRI contrast enhancing agent, and the level of binding is determined using MRI.

In another aspect, a method is provided for detecting tau pathology, the method comprising: contacting a biological sample with an effective amount of a targeting ligand-liposome conjugate comprising a targeting ligand that specifically binds to a cell surface marker of tau pathology, wherein the targeting ligand is conjugated to a liposome comprising a detectable label; washing the biological sample to remove unbound targeting ligand liposome conjugate; and detecting tau pathology in the biological sample by determining the amount of detectable label remaining in the biological sample. In some aspects, the biological sample is a sample containing neural cells.

In another aspect, a targeting composition is provided, the targeting composition comprising: a phospholipid linked to a polymer that is linked to a targeting ligand that specifically binds to a cell surface marker of tau pathology. In some aspects, the targeting ligand is an aptamer or stabilized aptamer. In some aspects, the targeting ligand is a thioaptamer. In some aspects, the aptamer or stabilized aptamer comprises a DNA nucleotide sequence selected from one or more of Tau_1 (SEQ ID NO: 5; DONGYBM), Tau_3 (SEQ ID NO: 6; MUSQD), Tau_9 (SEQ ID NO: 7), Tau_11 (SEQ ID NO: 8), Tau_10 (SEQ ID NO: 9), Tau_13 (SEQ ID NO: 10), Tau_8 (SEQ ID NO: 11), Tau_4 (SEQ ID NO: 12), Tau_17 (SEQ ID NO: 13), Tau_5 (SEQ ID NO: 14), Tau_21 (SEQ ID NO: 15), Tau_25 (SEQ ID NO: 16), Tau_7 (SEQ ID NO: 17), Tau_31 (SEQ ID NO: 18), Tau_42 (SEQ ID NO: 19), Tau_14 (SEQ ID NO: 20), Tau_19 (SEQ ID NO: 21), Tau_15 (SEQ ID NO: 22), Tau_56 (SEQ ID NO: 23), Tau_34 (SEQ ID NO: 24), Tau_23 (SEQ ID NO: 25), Tau_99 (SEQ ID NO: 26), and Tau_102 (SEQ ID NO: 27).

In some aspects, an aptamer or stabilized aptamer is provided, the aptamer or stabilized aptamer comprising a DNA nucleotide sequence selected from one or more of Tau_1 (SEQ ID NO: 5; DONGYBM), Tau_3 (SEQ ID NO: 6; MUSQD), Tau_9 (SEQ ID NO: 7), Tau_11 (SEQ ID NO: 8), Tau_10 (SEQ ID NO: 9), Tau_13 (SEQ ID NO: 10), Tau_8 (SEQ ID NO: 11), Tau_4 (SEQ ID NO: 12), Tau_17 (SEQ ID NO: 13), Tau_5 (SEQ ID NO: 14), Tau_21 (SEQ ID NO: 15), Tau_25 (SEQ ID NO: 16), Tau_7 (SEQ ID NO: 17), Tau_31 (SEQ ID NO: 18), Tau_42 (SEQ ID NO: 19), Tau_14 (SEQ ID NO: 20), Tau_19 (SEQ ID NO: 21), Tau_15 (SEQ ID NO: 22), Tau_56 (SEQ ID NO: 23), Tau_34 (SEQ ID NO: 24), Tau_23 (SEQ ID NO: 25), Tau_99 (SEQ ID NO: 26), and Tau_102 (SEQ ID NO: 27).

DETAILED DESCRIPTION

Figure 1A:
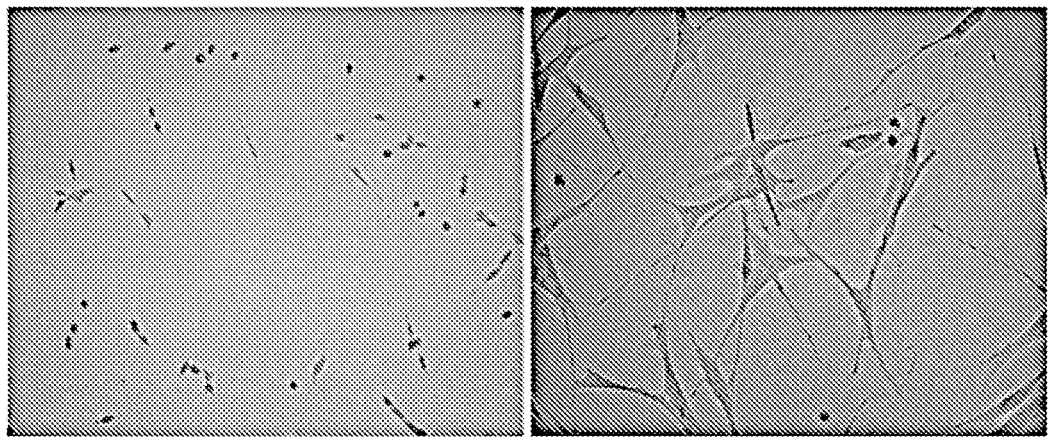
FIG. 1A shows (A) SH SY5Y cells (B) when treated with 30 µM retinoic acid (RA) for 10 days to differentiate to a neuron-like phenotype with axonal and dendritic structures. These cells develop long cell bodies and begin to form neurite-like processes.

This disclosure provides methods and compositions for detecting tau pathology. The compositions for detecting tau pathology comprise a targeting ligand that specifically binds to a cell surface marker of tau pathology, wherein the targeting ligand is linked to a liposome that includes an imaging agent. The compositions may be used in a method for imaging tau pathology in a subject that comprises administering to the subject an effective amount of the composition and imaging at least a portion of the subject to determine if that portion of the subject exhibits tau pathology. The compositions may also be used to detect tau pathology in biological samples obtained from a subject.

Definitions

Unless otherwise defined, all technical and scientific terms used herein have the same meaning as commonly understood by one of ordinary skill in the art to which this invention pertains. In case of conflict, the present specification, including definitions, will control.

Unless otherwise specified, "a," "an," "the," "one or more of," and "at least one" are used interchangeably. The singular forms "a", "an," and "the" are inclusive of their plural forms.

The recitations of numerical ranges by endpoints include all numbers subsumed within that range (e.g., 1 to 5 includes 1, 1.5, 2, 2.75, 3, 3.80, 4, 5, etc.).

The term "about," when referring to a value or to an amount of mass, weight, time, volume, concentration, or percentage is meant to encompass variations of +10% from the specified amount.

The terms "comprising" and "including" are intended to be equivalent and open-ended.

The phrase "consisting essentially of" means that the composition or method may include additional ingredients and/or steps, but only if the additional ingredients and/or steps do not materially alter the basic and novel characteristics of the claimed composition or method.

The phrase "selected from the group consisting of" is meant to include mixtures of the listed group and combinations thereof.

An "effective" or a "detectably effective amount" of a composition means an amount sufficient to detect the presence of cell surface markers associated with tau pathology or to yield an acceptable image using equipment that is available for clinical use. A detectably effective amount of a detecting or imaging agent may be administered in more than one injection. The detectably effective amount of the detecting or imaging agent may vary according to factors such as the degree of susceptibility of the individual, the age, sex, and weight of the individual, idiosyncratic responses of the individual, and the dosimetry. Detectably effective amounts of the detecting or imaging agent may also vary according to instrument and film-related factors. Optimization of such factors is well within the level of skill in the art. The amount of imaging agent used for diagnostic purposes, and the duration of the imaging study will depend upon the specific imaging agent used, the body mass of the patient, the nature and severity of the condition being treated, the nature of therapeutic treatments under which the patient has gone, and on the idiosyncratic responses of the patient. Ultimately, the attending physician will decide the amount of imaging agent to administer to each individual patient and the duration of the imaging study.

The term "diagnosis" may encompass determining the nature of a disease in a subject, as well as determining the severity and probable outcome of the disease or episode of the disease, the prospect of recovery (prognosis), or both. "Diagnosis" may also encompass diagnosis in the context of rational therapy, in which the diagnosis guides therapy, including initial selection of therapy, modification of therapy (e.g., adjustment of dose and/or dosage regimen), and the like.

The term antigen refers to a molecule or a portion of a molecule capable of being bound by a targeting ligand. An antigen is typically also capable of inducing an animal to produce an antibody capable of binding to an epitope of that antigen. An antigen can have one or more than one epitope. The specific reaction referred to above is meant to indicate that the antigen will react, in a highly selective manner, with its corresponding antibody and not with the multitude of other antibodies that can be evoked by other antigens.

The term epitope refers to that portion of any molecule capable of being recognized by, and bound by, a targeting ligand such as an aptamer. In general, epitopes comprise chemically active surface groupings of molecules, for example, amino acids or sugar side chains, and have specific three-dimensional structural and specific charge characteristics.

The phrase "specifically binds" refers to a targeting ligand binding to a target structure, wherein the targeting ligand binds the target structure, or a sub-unit thereof, but does not bind to a biological molecule that is not the target structure, or the targeting ligand at least binds preferentially to the target structure. Targeting ligands (e.g., thioaptamers) that specifically bind to a target structure or a sub-unit thereof may not cross-react with biological molecules that are outside of the target structure family.

The term "polynucleotide" refers to a nucleic acid sequence including DNA, RNA, and micro-RNA and can refer to markers that are either double-stranded or single-stranded. Polynucleotide can also refer to synthetic variants with alternative sugars such as locked nucleic acids.

Compositions for Identifying Tau Pathology

In one aspect, a composition for identifying tau pathology is provided, the composition comprising a targeting ligand that specifically binds to a cell surface marker of tau pathology, wherein the targeting ligand is linked to a liposome comprising an imaging agent.

In some aspects, the cell surface marker of tau pathology is a cell surface marker of tau hyperphosphorylation. Tau pathology refers to abnormal tau protein that results in taupathies. Tau pathology results from the hyperphosphorylation of tau protein. Normal tau contains 2-3 mol phosphate/mol protein, whereas hyperphosphorylated tau protein includes substantially higher levels of phosphate. Hyperphosphorylated tau leads to the formation of neurofibrillary tangles. Tau protein exists within the cell and is difficult to detect directly. However, certain cell surface markers (i.e., epitopes) are associated with the underlying tau pathology. In some aspects, these cell surface markers are epitopes that have been identified using the Cell-SELEX method, in which neurons exhibiting tau pathology or cell models of neurons are used as targets for target ligands (e.g., thioaptamers). In some aspects, the cell surface marker of tau pathology comprises a protein selected from KRT6A, KRT6B, HSP, and VIM.

Targeting Ligands

The term "targeting ligand" as used herein includes any molecule that can be linked to the liposome for the purpose of engaging a specific target and, in particular, for recognizing tau pathology. Examples of suitable targeting ligands include, but are not limited to, antibodies, antibody fragments, thioaptamers, aptamers, and stabilized aptamers. In some aspects, targeting ligands can be thioaptamers that specifically bind to cell surface markers for tau pathology.

The targeting ligands specifically bind to cells exhibiting tau pathology. Specific binding refers to binding that discriminates between the selected target and other potential targets and binds with substantial affinity to the selected target. Substantial affinity represents a targeting ligand having a binding dissociation constant of at least about $10^{-8}$ mol/m$^3$, but in other aspects, the targeting ligand can have a binding dissociation constant of at least about $10^{-9}$ mol/m$^3$, about $10^{-10}$ mol/m$^3$, about $10^{-11}$ mol/m$^3$, or at least about $10^{-12}$ mol/m$^3$.

In some aspects, the targeting ligand is an aptamer. An aptamer is a nucleic acid that binds with high specificity and affinity to a particular target molecule or cell structure, through interactions other than Watson-Crick base pairing. Suitable aptamers may be single stranded RNA, DNA, a modified nucleic acid, or a mixture thereof. The aptamers can also be in a linear or circular form. In some aspects, the aptamers are single stranded DNA, while in other aspects, they are single stranded RNA.

Aptamer functioning is unrelated to the nucleotide sequence itself, but rather is based on the secondary/tertiary structure formed by the polynucleotide, and aptamers are therefore best considered as non-coding sequences. Binding of a nucleic acid ligand to a target molecule is not determined by nucleic acid base pairing, but by the three-dimensional structure of the aptamer. In solution, the chain of nucleotides forms intramolecular interactions that fold the molecule into a complex three-dimensional shape. The shape of the nucleic acid ligand allows it to bind tightly against the surface of its target molecule. In addition to exhibiting remarkable specificity, nucleic acid ligands generally bind their targets with very high affinity, e.g., the majority of anti-protein nucleic acid ligands have equilibrium dissociation constants in the femtomolar to low nanomolar range.

The length of the aptamers suitable for use as targeting ligands is not particularly limited and includes aptamers including about 10 to about 200 nucleotides, about 100 nucleotides or less, about 50 nucleotides or less, about 40 nucleotides or less, or about 35 nucleotides or less. In some aspects, the aptamer has a size from about 15 to about 40 nucleotides. In addition, in almost all known cases, the various structural motifs that are involved in the non-Watson-Crick type of interactions involved in aptamer binding, such as hairpin loops, symmetric and asymmetric bulges, and pseudoknots, can be formed in nucleic acid sequences of 30 nucleotides or less.

In some aspects, the aptamers are stabilized aptamers that comprise a chemical modification to increase their stability. Modifications include, but are not limited to, those that provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2-position sugar modifications, 5-position pyrimidine modifications, 8-position purine modifications, modifications at exocyclic amines, substitution of 4-thiouridine, substitution of 5-bromo or 5-iodo-uracil, backbone modifications, phosphorothioate or alkyl phosphate modifications, methylations, unusual base-pairing combinations such as the isobases isocytidine and isoguanidine, and the like. Modifications can also include 3' and 5' modifications such as capping. In certain aspects, the nucleic acid ligands comprise RNA molecules that are 2'-fluoro (2'-F) modified on the sugar moiety of pyrimidine residues.

Suitable stabilized aptamers can further include nucleotide analogs, such as, for example, xanthine or hypoxanthine, 5-bromouracil, 2-aminopurine, deoxyinosine, or methylated cytosine such as 5-methylcytosine, N4-methoxydeoxycytosine, and the like. Also included are bases of polynucleotide mimetics, such as methylated nucleic acids, e.g., 2'-O-methRNA, peptide nucleic acids, locked nucleic acids, modified peptide nucleic acids, and any other structural moiety that acts substantially like a nucleotide or base, for example, by exhibiting base-complementarity with one or more bases that occur in DNA or RNA.

In some aspects, the stabilized aptamer comprises a thioaptamer. Thioaptamers are aptamers in which one or both of the non-bridging oxygen atoms have been substituted with sulfur. Oxygen-to-sulfur substitutions not only increases the stability of the aptamer, but in some cases also increases its binding affinity.

Typically, the targeting ligand (e.g., aptamer) is linked to a liposome comprising an imaging agent. However, the aptamers themselves are novel and useful. Examples of suitable aptamers include those comprising a DNA nucleotide sequence selected from, and in some instances, selected from the group consisting of: Tau_1 (SEQ ID NO: 5), Tau_3 (SEQ ID NO: 6), Tau_9 (SEQ ID NO: 7), Tau_11 (SEQ ID NO: 8), Tau_10 (SEQ ID NO: 9), Tau_13 (SEQ ID NO: 10), Tau_8 (SEQ ID NO: 11), Tau_4 (SEQ ID NO: 12), Tau_17 (SEQ ID NO: 13), Tau_5 (SEQ ID NO: 14), Tau_21 (SEQ ID NO: 15), Tau_25 (SEQ ID NO: 16), Tau_7 (SEQ ID NO: 17), Tau_31 (SEQ ID NO: 18), Tau_42 (SEQ ID NO: 19), Tau_14 (SEQ ID NO: 20), Tau_19 (SEQ ID NO: 21), Tau_15 (SEQ ID NO: 22), Tau_56 (SEQ ID NO: 23), Tau_34 (SEQ ID NO: 24), Tau_23 (SEQ ID NO: 25), Tau_99 (SEQ ID NO: 26), and Tau_102 (SEQ ID NO: 27).

In some aspects, the aptamers are positioned between two primer nucleotide sequences that facilitate amplification of the aptamer sequence, e.g., by Polymerase Chain Reaction (PCR). For example, in some aspects, the DNA nucleotide sequence of the aptamer is positioned between the sequences GATATGTCTAGAGCCTCAGATCA (SEQ ID NO: 1) and CGGAGTTATGTTAGCAGTAGC (SEQ ID NO: 2). In other aspects, the DNA nucleotide sequence of the aptamer is positioned between the sequences CGC TCG ATA GAT CGA GCT TCG (SEQ ID NO: 3) and GTC GAT CAC GCT CTA GAG CAC (SEQ ID NO: 4).

Validation of Cell Surface Changes in Hyperphosphorylative Conditions

Figure 1B:
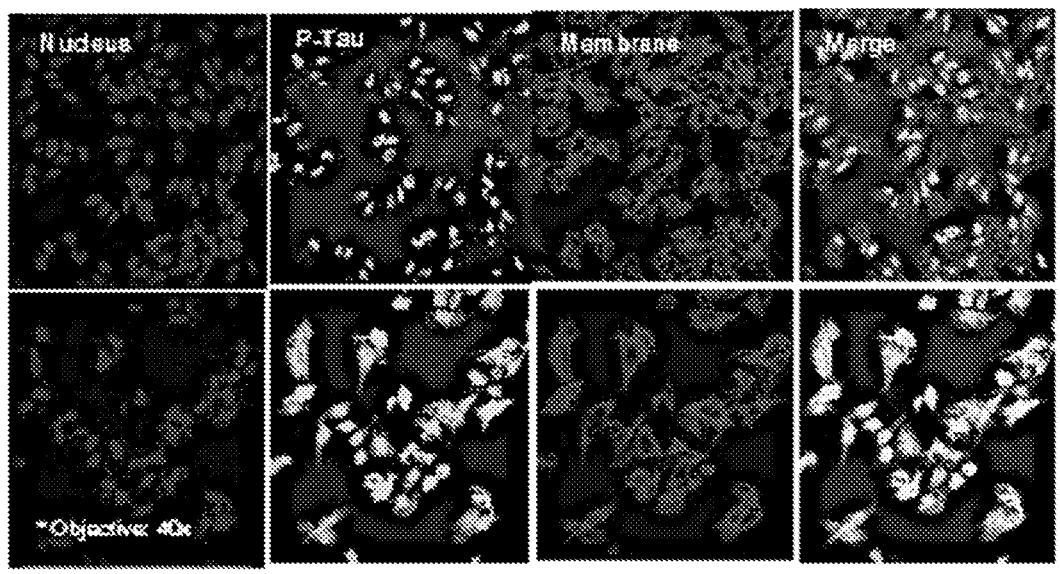
FIG. 1B shows the SH SY5Y cells after treatment with okadaic acid (OA), demonstrating that the cells avidly phosphorylate tau. The upper row shows that the differentiated cells exhibit pTau Thr205/Ser202 (an early phase of phosphorylation) mostly in the perinuclear region. The lower row shows that after exposure to 30 nM OA for 24 h, the cells exhibit significant levels of pTau Ser396 (a late stage of phosphorylation) throughout the cytoplasm.
Figure 1C:
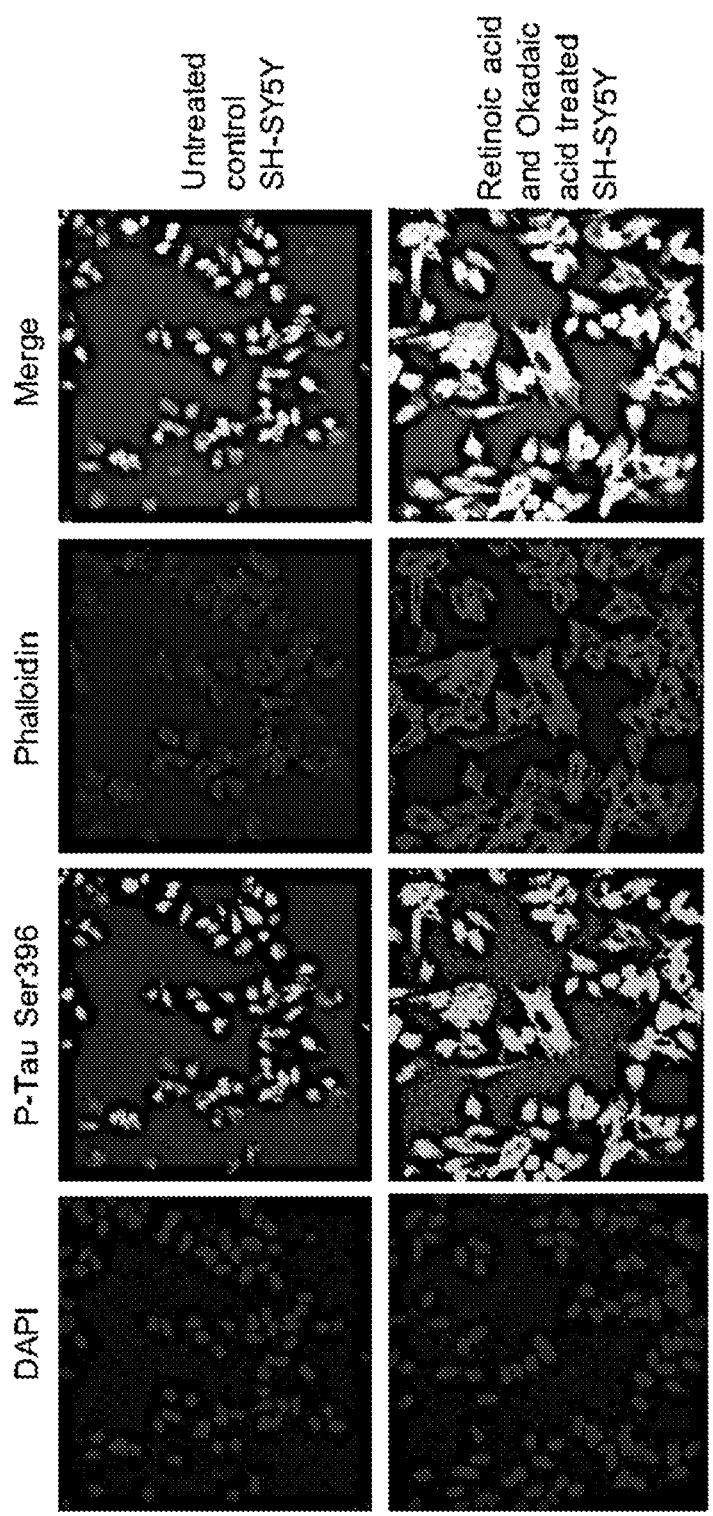
FIG. 1C shows the presence of p-tau396 in SHSY5Y cells in hyperphosphorylative conditions. The cells were differentiated with 30 UM RA for 10 days and exposed to 30 nM OA for 24 h. Under these hyperphosphorylative conditions, tau is over-expressed and hyperphosphorylated.

SH-SY5Y, a human neuroblastoma cell line that can be differentiated into neuron-like cells by changes in culture medium, was used to model cell-surface changes under hyperphosphorylative conditions. As depicted in FIGS. 1A-1C, RA was used to induce cell differentiation marked by temporal changes in morphology including the formation and lengthening of neurites and with a strong increase in levels of intracellular tau. Imbalance in the kinase and phosphatase activity leading to hyperphosphorylation, simulating early stages of tauopathies, was induced by the use of a cell permeable neurotoxin OA (30 nM, 24 h) and confirmed by the increase in phosphorylated tau S396 (see FIGS. 1B and 1C). In parallel experiments, a milder agent, excitotoxin quinolinic acid (QA) 1 µM, was used to induce hyperphosphorylation.

RPPA analysis conducted on lysates of both RA-treated and untreated SH-SY5Y cells rendered hyperphosphorylative by either OA (30 nM, 24 h) or QA (1 µM, 24 h) demonstrated marked changes in hyperphosphorylative cells. Ninety-eight unphosphorylated proteins and 36 phosphorylated proteins were tested that showed significant change in their expression under different conditions. Uniprot protein associations showed that 44 cell-membrane associated proteins, 10 peripheral membrane, and 12 single-pass membrane proteins were significantly altered under hyperphosphorylative conditions. In summary, RPPA analysis demonstrated marked cell surface changes in hyperphosphorylative cells including over-expression of cell surface receptors.

Screening for Aptamers That Bind Cells in a Hyperphosphorylative State

Aptamer screening was performed using the cell-SELEX approach on differentiated SH-SY5Y cells in a hyperphosphorylative state. FIGS. 2A-2E describe how cell-SELEX was used to identify biomarkers of onset the of AD. OA treated differentiated SH-SY5Y cells were used as a surrogate for hyperphosphorylative neurons to screen DNA aptamers that specifically recognize the differences between the surfaces of treated and untreated cells, using the cell-SELEX methodology modified to capture membrane binding aptamers. A total of 26 cell SELEX cycles were performed. To remove thioaptamers that bound common cell surface molecules not specific to the hyperphosphorylative state, a negative selection was introduced at cycles 12 and 13 using differentiated, non-hyperphosphorylative cells (i.e., without OA treatment). Anticipating that selected thioaptamers would be systemically delivered as nanoparticle imaging agents, the primary toxicity of which is driven by hepatocyte uptake, another round of negative selection was conducted at cycles 20 and 21 using a hepatocyte cell-line THLE-3 to remove oligonucleotides that exhibited enhanced uptake by hepatocytes.

Tau 1 and Tau 3 Aptamers Specifically Bind Hyperphosphorylative Cells

Figure 2A:
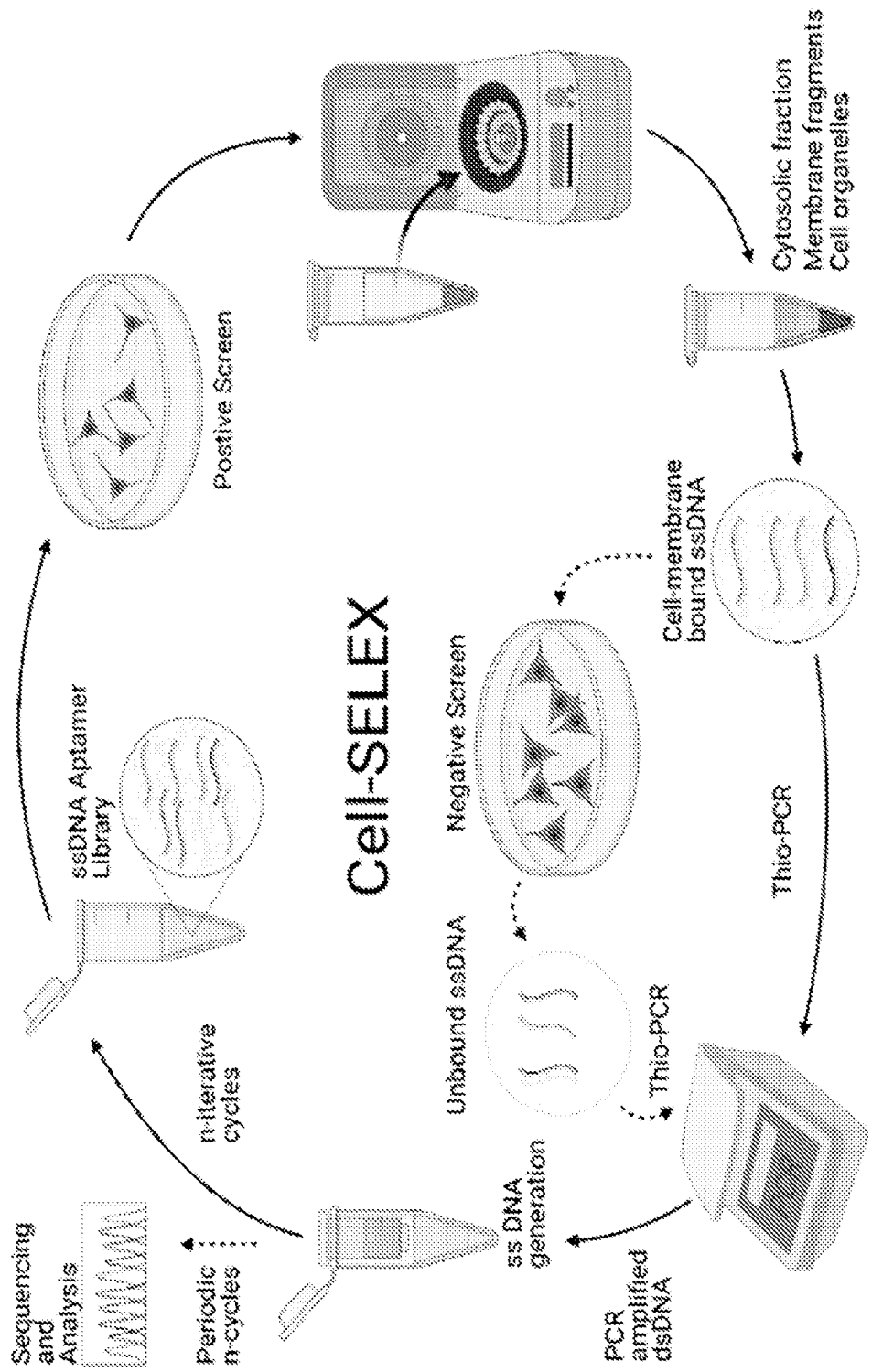
FIG. 2A shows a pictorial representation of the cell-SELEX process.
Figure 2B:
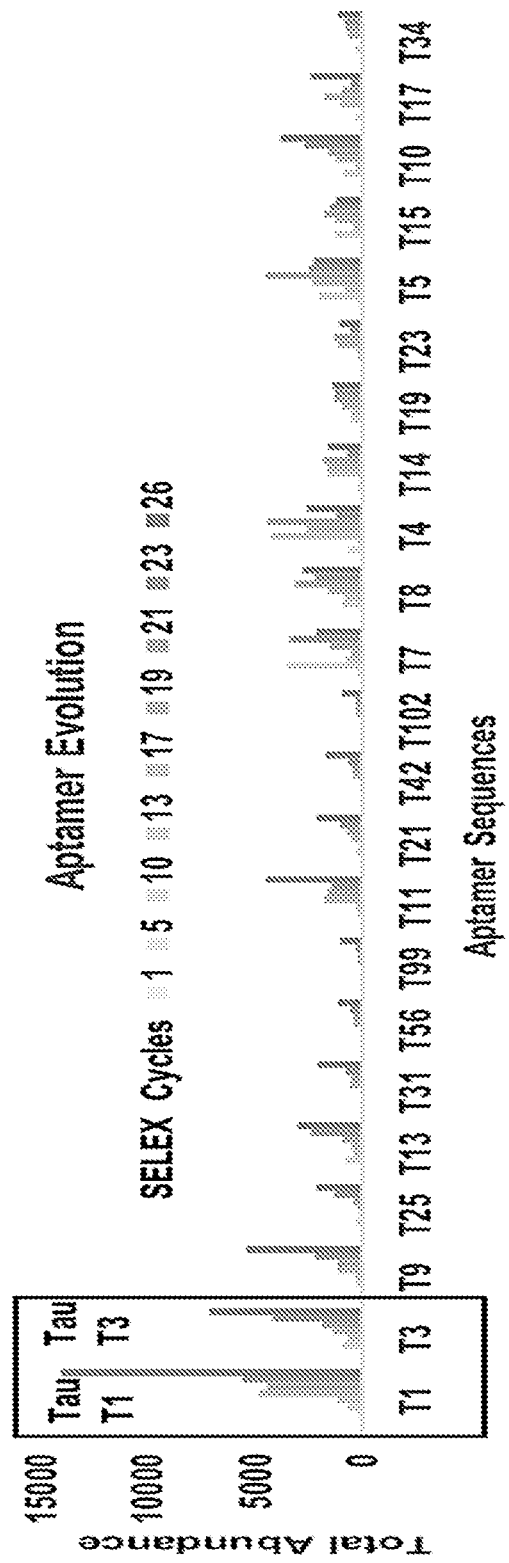
FIG. 2B shows the abundance of the top 23 sequences from SELEX cycle 1-26 depicting their evolution. The fractions are low until about cycle 10, when they increase sharply. The abundance of Tau_1 (SEQ ID NO: 5; DONGYBM) and Tau_3 (SEQ ID NO: 6; MUSQD) continually increase with increasing cycle number.
Figure 2C:
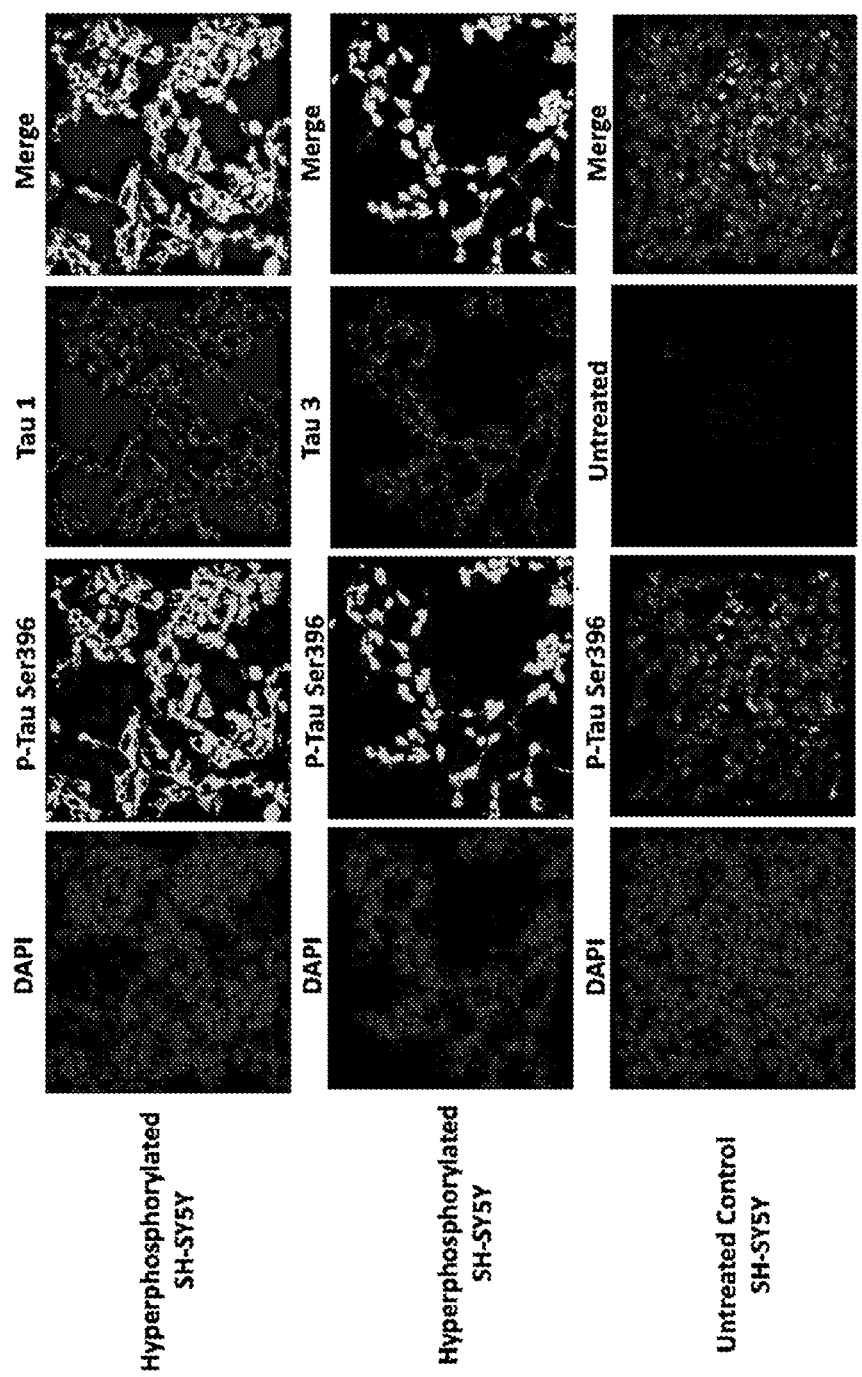
FIG. 2C shows hyperphosphorylated (OA) SH-SY5Y cells stained with 50 nM Cy5 labelled Tau_1 (SEQ ID NO: 5; DONGYBM) or Tau_3 (SEQ ID NO: 6; MUSQD) aptamer for 2 h at 4° C.
Figure 2D:
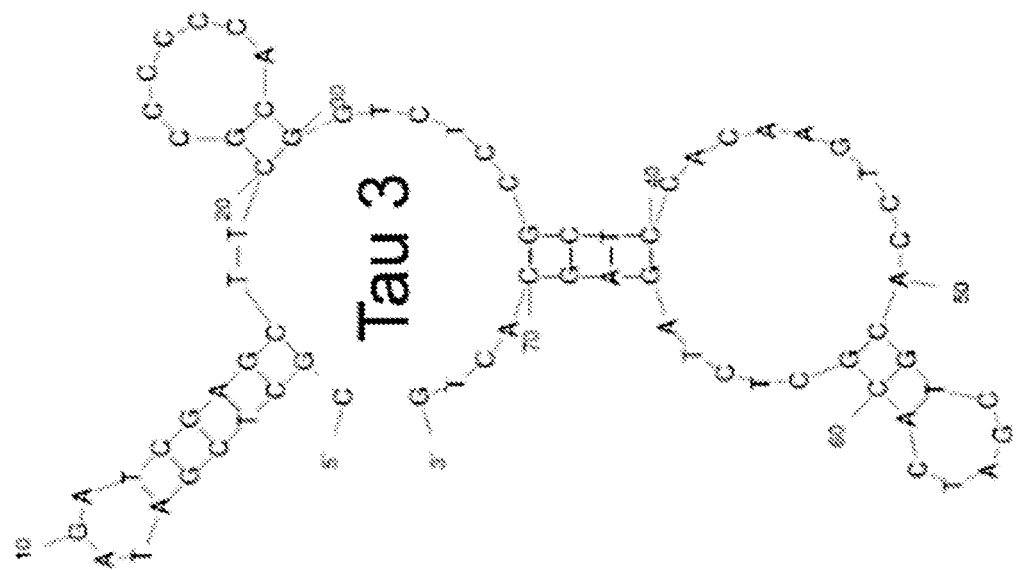
FIG. 2D shows Tau_1 (SEQ ID NO: 5; DONGYBM) and Tau_3 (SEQ ID NO: 6; MUSQD) secondary structures using Mfold.
Figure 2D:
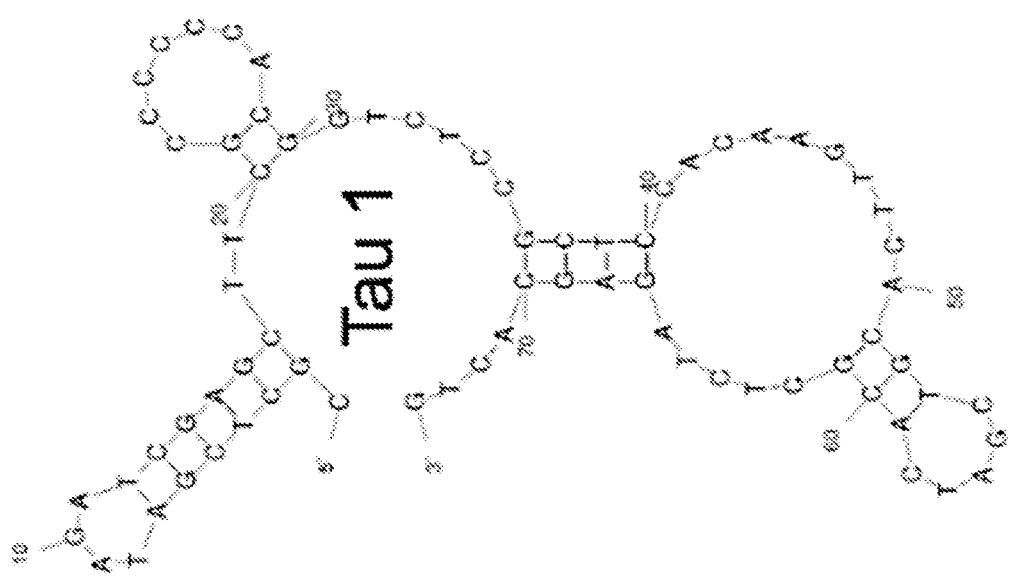
Figure 2E:
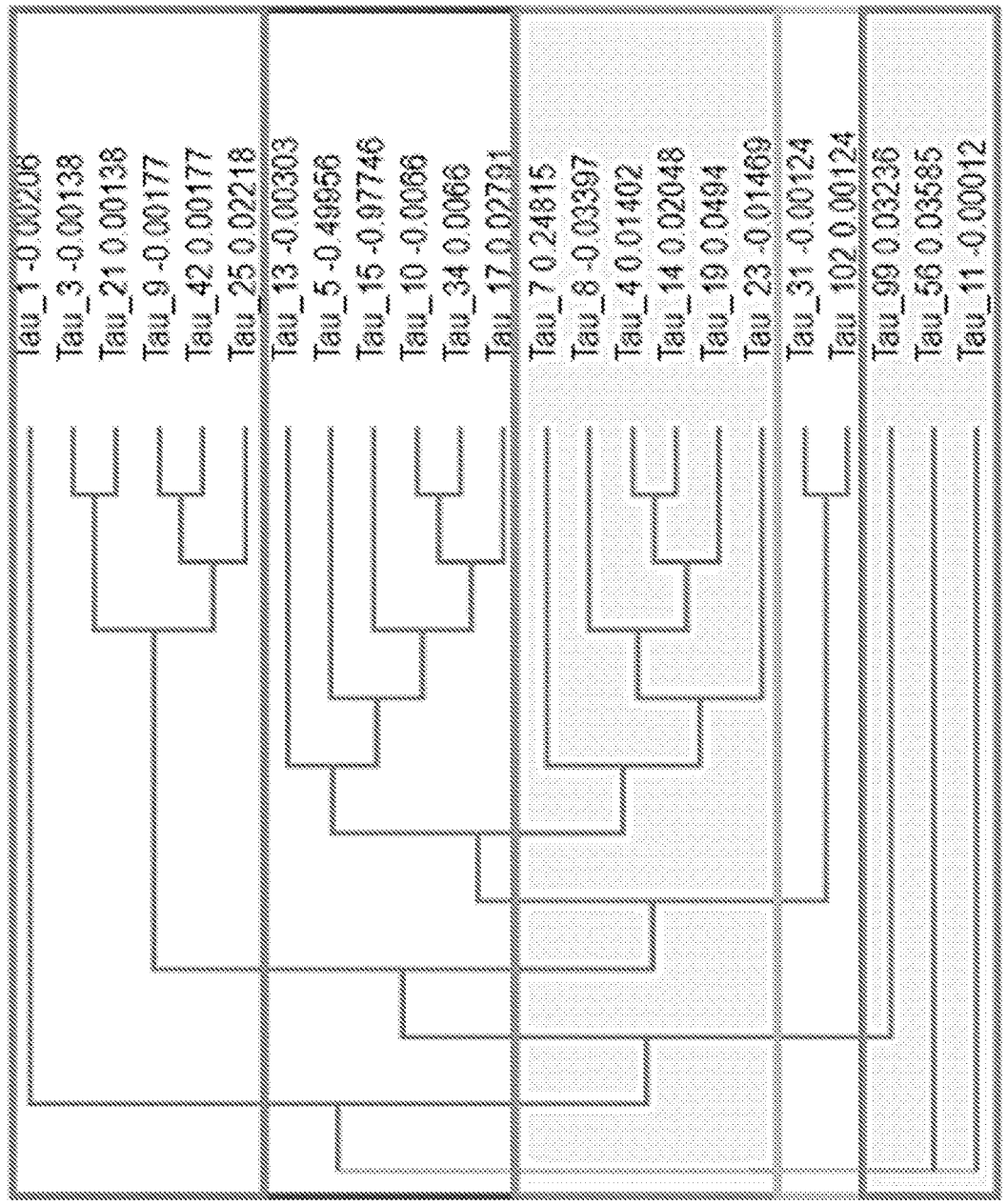
FIG. 2E shows a cladogram showing the relationship between the top 23 tau aptamer sequences and the aptamer families.

Sequencing of all the selected pools using the Ion Torrent sequencing platform revealed the evolution of families of DNA sequences, with enrichment particularly evident after 10 rounds of SELEX. Negative selection eliminated certain sequences that were not specific to the hyperphosphorylative state or have a propensity for hepatocyte uptake. However, the relative abundance of key sequences increased steadily throughout the whole process. The 23 most abundant sequences at round 26 were identified, and their abundance throughout the SELEX process as calculated using AptaAligner is shown in FIG. 2B. The sequence Tau_1 (SEQ ID NO: 5; DONGYBM) was the most prevalent at cycle 26, representing 20.6% of the thioaptamers present. A single base difference from this sequence, Tau_3 (SEQ ID NO: 6; MUSQD), was the second most represented sequence (10.4%). Binding studies using Cy5-labeled Tau_1 (SEQ ID NO: 5; DONGYBM) or Tau_3 (SEQ ID NO: 6; MUSQD) incubated with 99 hyperphosphorylative SH-SY5Y cells demonstrated elevated binding levels with the hyperphosphorylative cells (FIG. 2C). The secondary structure of the aptamers Tau_1 (SEQ ID NO: 5; DONGYBM) and Tau_3 (SEQ ID NO: 6; MUSQD) calculated using mfold is shown in FIG. 2D. The sequences present at the final round were grouped by hierarchical clustering and sequence homology using the multiple sequence alignment code MAFFT showing five distinct families, which were also presented as a cladogram (using the Clustal Omega) showing the common ancestry between these five aptamers families (FIG. 2E).

Figure 3:
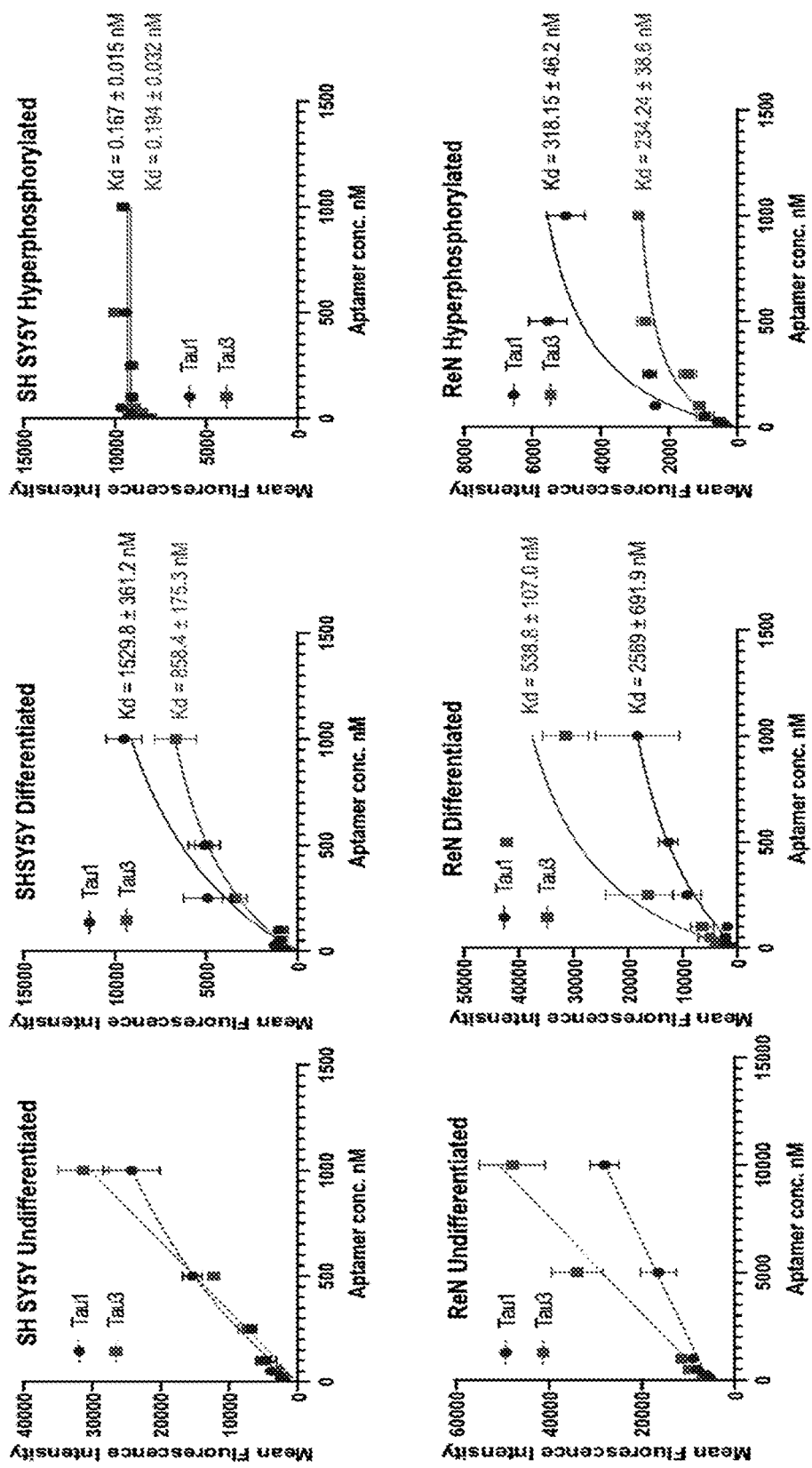
FIG. 3 shows the saturation binding curves generated using Cy5 labeled Tau_1 (SEQ ID NO: 5; DONGYBM) and Tau_3 (SEQ ID NO: 6; MUSQD) after serial dilution of aptamer solutions with target hyperphosphorylated and non-target differentiated and undifferentiated SH-SY5Y and ReN-VM cells.

The apparent equilibrium dissociation constants ($Kd_{app}$) were measured by serial dilution of aptamer solutions with target hyperphosphorylated, non-target differentiated, and undifferentiated SH-SY5Y cells. The affinity of these aptamers was also tested with another immortal neural progenitor stem cell line, ReN-VM, in hyperphosphorylative and non-hyperphosphorylative conditions. The $Kd_{app}$ for Tau_1 (SEQ ID NO: 5; DONGYBM) and Tau_3 (SEQ ID NO: 6; MUSQD) with hyperphosphorylated SH SY5Y cells is 0.167±0.015 nM and 0.194±0.032 nM; and for the ReN-VM cells 318.15±46.2 nM and 234.24±38.6 nM, respectively (FIG. 3).

Sequencing

After identification, the aptamers may be sequenced. Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, the 454 sequencing method, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLID sequencing.

Sequencing may be by any method known in the art. See for example Sanger et al. (Proc Natl Acad Sci USA, 74 (12): 5463 67, 1977), Maxam et al. (Proc. Natl. Acad. Sci., 74:560-564, 1977), and Drmanac, et al. (Nature Biotech., 16:54-58, 1998), which references describe example conventional ensemble sequencing techniques. Also see Lapidus et al. (U.S. Pat. No. 7,169,560), Quake et al. (U.S. Pat. No. 6,818,395), Harris (U.S. Pat. No. 7,282,337), Quake et al. (U.S. patent application number 2002/0164629), and Braslaysky, et al., (PNAS (USA), 100:3960-3964, 2003), which references describe example single molecule sequencing by synthesis techniques. The contents of each of these references is incorporated by reference herein in its entirety.

Several aptamers are disclosed herein that specifically bind to tau pathology. Examples of these aptamers are described in Table 1. Accordingly, in some aspects, the aptamer or stabilized aptamer comprises a DNA nucleotide sequence selected from, including selected from the group consisting of: Tau_1 (SEQ ID NO: 5; DONGYBM), Tau_3 (SEQ ID NO: 6; MUSQD), Tau_9 (SEQ ID NO: 7), Tau_11 (SEQ ID NO: 8), Tau_10 (SEQ ID NO: 9), Tau_13 (SEQ ID NO: 10), Tau_8 (SEQ ID NO: 11), Tau_4 (SEQ ID NO: 12), Tau_17 (SEQ ID NO: 13), Tau_5 (SEQ ID NO: 14), Tau_21 (SEQ ID NO: 15), Tau_25 (SEQ ID NO: 16), Tau_7 (SEQ ID NO: 17), Tau_31 (SEQ ID NO: 18), Tau_42 (SEQ ID NO: 19), Tau_14 (SEQ ID NO: 20), Tau_19 (SEQ ID NO: 21), Tau_15 (SEQ ID NO: 22), Tau_56 (SEQ ID NO: 23), Tau_34 (SEQ ID NO: 24), Tau_23 (SEQ ID NO: 25), Tau_99 (SEQ ID NO: 26), and Tau_102 (SEQ ID NO: 27). In a further aspect, the aptamer or stabilized aptamer comprises the DNA nucleotide sequence Tau_1 (SEQ ID NO: 5; DONGYBM), Tau_3 (SEQ ID NO: 6; MUSQD), or both.

TABLE 1

Aptamers that Specifically Bind to Tau Pathology

| Identifier | Nucleotide Sequence | SEQ ID NO |
|---|---|---|
| Tau_1 | CCCCCCACGGTCTCCGCTCCACAAGTTCAC | SEQ ID NO: 5 |
| Tau_3 | CCCCCCACGGTCTCCGCTCCACAAGTCCAC | SEQ ID NO: 6 |
| Tau_9 | CCCCCCACGGTCTCCGCTCCACAGGTTCAC | SEQ ID NO: 7 |
| Tau_11 | CCCCCCCACGGTCTCCGCTCCACAAGTTCA | SEQ ID NO: 8 |
| Tau_10 | CTCGTGGGTGTGTGGTGGTGTTGTTGTGTG | SEQ ID NO: 9 |
| Tau_13 | CCCCCCACGGTCTCCGCTCCACAAGCCCAC | SEQ ID NO: 10 |
| Tau_8 | CTCGTCCCACCACAACATCATCTCAACGCC | SEQ ID NO: 11 |
| Tau_4 | CTCGTCCCACCACAACATTATCTCAACGCC | SEQ ID NO: 12 |

TABLE 1-continued

Aptamers that Specifically Bind to Tau Pathology

| Identifier | Nucleotide Sequence | SEQ ID NO |
|---|---|---|
| Tau_17 | CTCGTGGGTGTACGGTGGTGTTGTTGTGTG | SEQ ID NO: 13 |
| Tau_5 | CTCCGACGGGATGTTCGATGAGCACACACT | SEQ ID NO: 14 |
| Tau_21 | CCCCCCCACGGTCTCCGCTCCACAAGTCCA | SEQ ID NO: 15 |
| Tau_25 | CCCCCCACGGTCTCCGCTCCACAGGTCCAC | SEQ ID NO: 16 |
| Tau_7 | CCCCCATTGGCTCCGCTCCACACAGCTTCA | SEQ ID NO: 17 |
| Tau_31 | CCCCCCACGGTCTCCGCTCCACAAGCTCAC | SEQ ID NO: 18 |
| Tau_42 | CCCCCCCACGGTCTCCGCTCCACAGGTTCA | SEQ ID NO: 19 |
| Tau 14 | CTCGTCCCACCACAACATTGTCTCAACGCC | SEQ ID NO: 20 |
| Tau_19 | CTCGTCCCACCACAACACCATCTCAACGCC | SEQ ID NO: 21 |
| Tau_15 | CTCCGACGGGTGTTCGATGAGCACACACT | SEQ ID NO: 22 |
| Tau_56 | CCCCCCGCGGTCTCCGCTCCACAAGTTCAC | SEQ ID NO: 23 |
| Tau_34 | TGGGTGTGTGGTGGTGTTGTTGTGTGGGTG | SEQ ID NO: 24 |
| Tau_23 | CTCGCCCCACCACAACATCATCTCAACGCC | SEQ ID NO: 25 |
| Tau_99 | CCCCCCACGGTCTCCGCTCCACAAGTTCGC | SEQ ID NO: 26 |
| Tau_102 | CCCCCCCACGGTCTCCGCTCCACAAGCTCA | SEQ ID NO: 27 |

Targeting Ligand Conjugates

In some aspects, the targeting ligands (e.g., aptamers) are linked to a liposome or other vehicles for targeted delivery of an imaging or detecting agent. For example, imaging or detecting agents can be encapsulated within the liposome. Employing such techniques, the tau pathology-specific aptamers conjugated to a liposomal vesicle can provide targeted delivery of imaging or detecting agents to cells expressing tau pathology. In some aspects, a single targeting ligand is linked to a liposome. In other aspects, targeting ligands (e.g., Tau_1 (SEQ ID NO: 5; DONGYBM) and Tau_3 (SEQ ID NO: 6; MUSQD)) are linked to the liposome.

The term "liposome" as used herein indicates a vesicular structure comprised of lipids. The lipids typically have a tail group comprising a long hydrocarbon chain and a hydrophilic head group. The lipids are arranged to form a lipid bilayer (i.e., membrane) with an inner aqueous environment suitable to contain an agent (e.g., imaging agent) to be delivered. Such liposomes present an outer surface that may comprise suitable targeting ligands that specifically bind to cell surface markers of tau pathology. A suitable liposome platform may be, for example, the "ADx" platform from Alzeca Biosciences, comprising hydrogenated soy L-α-phosphatidylcholine (HSPC), cholesterol (Chol), 1,2-distearoyl-sn-glycero-3-phosphoethanolamine-N-(methoxy (polyethylene glycol)-2000) (DSPE-mPEG2000), and Gd(III)-DSPE-DOTA (the macrocyclic gadolinium imaging moiety, Gd(III)-DOTA, conjugated to a phospholipid, 1,2-Distearoyl-sn-glycero-3-phosphorylethanolamine, DSPE), as well as the entity used to conjugate the targeting ligand, DSPE-PEG-3400 (1,2-distearoyl-sn-glycero-3-phosphoethanolamine-N-[maleimide (polyethylene glycol)-3400]). See, e.g., U.S. Pat. No. 11,116,854, International Patent Publication No. WO2020154623A1, and International Patent Publication No. WO2021163585A1, each of which is incorporated by reference herein in its entirety.

In some aspects, the membrane of the liposome may comprise at least three types of phospholipids. The membrane may comprise a first phospholipid, which may be unmodified. Suitable first phospholipids include those disclosed in U.S. Pat. Nos. 7,785,568 and 10,537,649, each of which is incorporated by reference herein in its entirety. In one aspect, the first phospholipid is HSPC. The membrane may include a second phospholipid that may be derivatized with a first polymer. Suitable polymer-derivatized second phospholipids include those disclosed in U.S. Pat. Nos. 7,785,568 and 10,537,649. In one aspect, the second phospholipid that is derivatized with a first polymer is DSPE-mPEG2000. The membrane may include a third phospholipid that is derivatized with a second polymer, the second polymer ultimately being conjugated to the targeting ligand. Suitable polymer-derivatized third phospholipids include those disclosed in U.S. Pat. Nos. 7,785,568 and 10,537,649. One aspect, the third phospholipid that is derivatized with a second polymer is DSPE-PEG-3400.

In some aspects, the membrane may comprise a sterically bulky excipient that is capable of stabilizing the liposome. Suitable excipients include those disclosed in U.S. Pat. Nos. 7,785,568 and 10,537,649. In one aspect, the sterically bulky excipient that is capable of stabilizing the liposome is cholesterol.

In some aspects, the phospholipid moiety in the phospholipid-polymer-targeting ligand conjugate may be represented by the following structural formula:

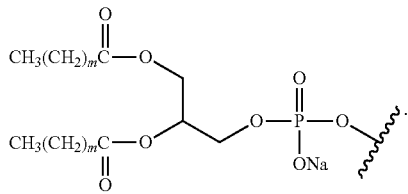

The variable m may be one of: 12, 13, 14, 15, 16, 17, or 18. For example, m may be 14 or 16. In various aspects, the phospholipid moiety in any of the first phospholipid, the second phospholipid, and the phospholipid-polymer-targeting ligand conjugate may be one of: HSPC, DPPC, DSPE, DSPC, or DPPE.

In some aspects, the polymer moiety in the phospholipid-polymer-targeting ligand conjugate is a polyol. Structural units forming polymers containing polyols comprise monomeric polyols such as pentaerythritol, ethylene glycol, and glycerin. Example polymers containing polyols comprise polyesters, polyethers, and polysaccharides. Example suitable polyethers include, but are not limited to, diols, such as diols with the general formula HO—(CH2CH2O)p-H with p≥1, for example, polyethylene glycol, polypropylene glycol, and poly(tetramethylene ether) glycol. Suitable polysaccharides include, but are not limited to, cyclodextrins, starch, glycogen, cellulose, chitin, and beta-Glucans. Suitable polyesters include, but are not limited to, polycarbonate, polybutyrate, and polyethylene terephthalate, all terminated with hydroxyl end groups. Example polymers containing polyols comprise polymers of about 500,000 Da or less molecular weight, including from about 300 to about 100,000 Da.

In some aspects, the polymer moiety in the phospholipid-polymer-targeting ligand conjugate comprises a hydrophilic poly(alkylene oxide) polymer. The hydrophilic poly(alkylene oxide) may include between about 10 and about 100 repeat units, and having, e.g., a molecular weight ranging from about 500-10,000 Da. The hydrophilic poly(alkylene oxide) may comprise, for example, poly(ethylene oxide), poly(propylene oxide), and the like. The polymer moiety in the phospholipid-polymer-targeting ligand conjugate may be conjugated to the phospholipid moiety via an amide or carbamate group. The polymer moiety in the phospholipid-polymer-targeting ligand conjugate may be conjugated via an amide, carbamate, poly(alkylene oxide), triazole, combinations thereof, and the like. For example, the polymer moiety in the phospholipid-polymer-targeting ligand conjugate may be represented by one of the following structural formulas:

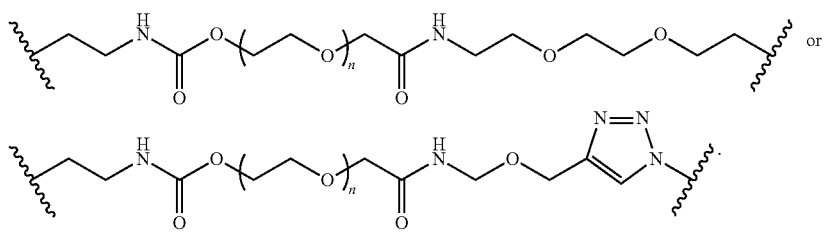

The variable n may be any integer from about 10 to about 100, for example, about 60 to about 100, about 70 to about 90, about 75 to about 85, or about 77.

In some aspects, the phospholipid-polymer moiety in the phospholipid-polymer-targeting ligand conjugate may be represented by one of the following structural formulas:

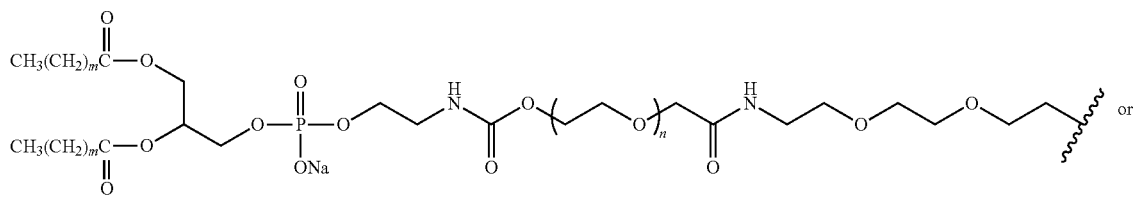

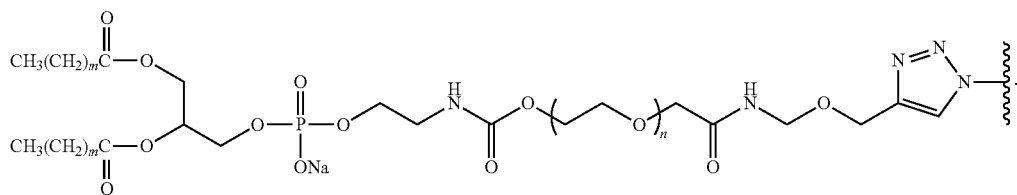

The variable n may be any integer from about 10 to about 100, for example, about 60 to about 100, about 70 to about 90, about 75 to about 85, or about 77. The variable m may be one of: 12, 13, 14, 15, 16, 17, or 18. For example, n may be 77 and m may be 14. In another example, n may be 77 and m may be 16.

In some aspects, the third phospholipid that is derivatized with a second polymer, the second polymer being conjugated to the targeting ligand, may comprise:

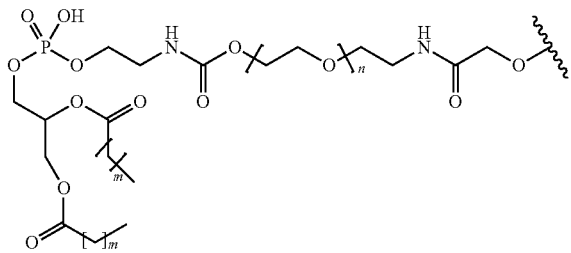

or a salt (e.g., an ammonium phosphate salt) thereof. In some aspects, the variable n may be any integer from about 10 to about 100, for example, about 60 to about 100, about 70 to about 90, about 75 to about 85, about 77, or about 79. The variable m may be one of: 12, 13, 14, 15, 16, 17, or 18. For example, n may be 77, and m may be 14; n may be 79, and m may be 14; n may be 77, and m may be 16; and n may be 79, and m may be 16.

The targeting ligands (e.g., aptamers) may be connected to one or more polymer (e.g. PEG) moieties of the phospholipid-polymer-targeting ligand conjugate, with or without one or more linkers. The PEG moieties may be any type of PEG moiety (linear, branched, multiple branched, star shaped, comb shaped, or a dendrimer) and have any molecular weight. The same or different linkers or no linkers may be used to connect the same or different PEG moieties to an aptamer. Commonly known linkers include, but are not limited to, amines, thiols, and azides, and can include a phosphate group. For example, in some aspects, the targeting ligand is linked to polyethylene glycol that is conjugated to a phospholipid that associates with the liposome.

In some aspects, the liposomes include a membrane, the membrane comprising: a first phospholipid selected from HSPC, DPPC, DSPE, DSPC, and DPPE; cholesterol; DPPC, DSPE, DSPC, and/or DPPE derivatized with PEG; DPPC, DSPE, DSPC, and/or DPPE derivatized with PEG and a targeting ligand that specifically binds to a cell surface marker of tau pathology; and an imaging agent that is encapsulated by or bound to the membrane. In further aspects, the targeting ligand is a thioaptamer, and the imaging agent is an MRI contrast enhancing agent.

In some aspects, a targeting composition is provided. In some aspects, the targeting composition includes a phospholipid linked to a polymer that is linked to a targeting ligand that specifically binds to a cell surface marker of tau pathology. The phospholipid can be any of the phospholipids described herein. In some aspects, the phospholipid comprises one or more of DPPC, DSPE, DSPC, and DPPE. Likewise, the polymer can be any of the polymers (e.g., polyols) described herein. In some aspects, the polymer is polyethylene glycol.

Imaging or Detecting Agents

The composition for detecting tau pathology described herein may include an imaging or detecting agent. The imaging or detecting agent is generally associated with the liposome portion of the composition. The imaging or detecting agent can be held within the liposome, or it can be conjugated to the liposome. In one aspect, the imaging or detecting agent is linked to a polymer that is linked to a phospholipid that associates with the membrane forming the liposome.

The liposomal composition comprises a macrocyclic Gd-based imaging agent. In some aspects, the macrocyclic gadolinium-based imaging agent comprises Gd(III)-DOTA conjugated to a phospholipid, e.g.:

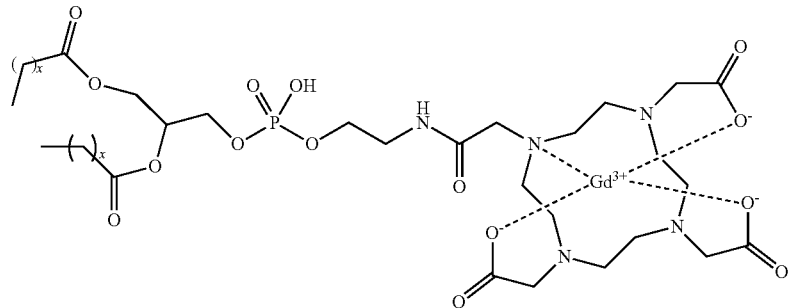

or a salt (e.g., a sodium salt) thereof. In some aspects, the variable x may be one of: 12, 13, 14, 15, 16, 17, or 18. In one aspect, the variable x is 16 and the conjugate is Gd(III)-DOTA-DSPE. Preparation of Gd(III)-DOTA-DSPE is described in U.S. Pat. No. 11,116,854.

In other aspects, the macrocyclic gadolinium-based imaging agent comprises:

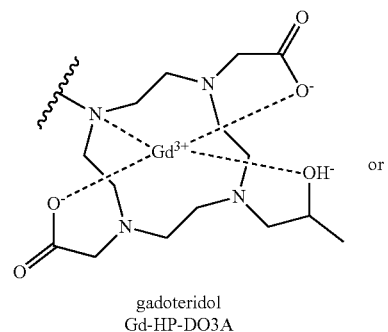

gadoteridol
Gd-HP-DO3A

-continued

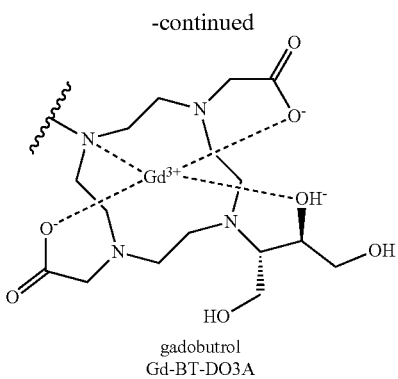

gadobutrol
Gd-BT-DO3A

In one aspect, the imaging or detecting agent is linked to a polymer that is linked to a phospholipid that associates with the membrane forming the liposome comprises Gd(III)-DOTA-DSPE.

In some aspects, the composition for detecting tau pathology includes a detecting agent. Examples of detecting agents include GFP, biotin, cholesterol, dyes such as fluorescence dyes, electrochemically active reporter molecules, and compositions comprising radioactive residues, such as radionuclides suitable for PET (positron emission tomography) detection, e.g., 18F, 11C, 13N, 15O, 82Rb or 68Ga.

In some aspects, the composition for detecting tau pathology comprises an imaging agent. Imaging agents differ from detecting agents in that they not only indicate the presence of tau pathology but are suitable for use with imaging methods that allow an image of a region of tissue exhibiting the tau pathology to be created and displayed. Examples of imaging agents include near infrared imaging agents, positron emission tomography imaging agents, single-photon emission tomography agents, fluorescent compositions, radioactive isotopes, and MRI contrast agents.

In some aspects, the imaging agent is an MRI contrast enhancing agent. Disease detection using MRI is often difficult because areas of disease have similar signal intensity compared to surrounding healthy tissue. In the case of MRI, the imaging agent can also be referred to as a contrast agent. The MRI contrast enhancing agent may be a nonradioactive MRI contrast enhancing agent that may be at least one of encapsulated by or bound to the membrane. For example, the nonradioactive MRI contrast enhancing agent may be both encapsulated by and bound to the membrane, e.g., to provide a dual contrast agent liposome. The liposomal composition may be characterized by a per-particle relaxivity in mM$-1$s$-1$ of at least about one or more of about: 100,000, 125,000, 150,000, 165,000, 180,000, 190,000, and 200,000. Detecting the liposomal formulation may include detecting using MRI in a magnetic field range of, for example, between about 1 T to about 3.5 T, or about 1.5 to about 3 T. The nonradioactive MRI contrast enhancing agent may include gadolinium. Suitable nonradioactive MRI contrast enhancing agent may include Gd(III)-DOTA-DSPE and (diethylenetriaminepentaacetic acid)-bis(stearylamide), gadolinium salt (Gd-DTPA-BSA). Gadolinium paramagnetic chelates such as GdDTPA, GdDOTA, GdHPDO3A, GdDTPA-BMA, and GdDTPA-BSA are also suitable known MRI contrast agents. See U.S. Pat. No. 5,676,928 issued to Klaveness et al., which is incorporated by reference herein in its entirety.

Methods of Imaging or Detecting Tau Pathology

In another aspect, a method is provided for imaging tau pathology in a subject. The method comprises administering to the subject a detectably effective amount of a targeting ligand-liposome conjugate comprising a targeting ligand that specifically binds to a cell surface marker of tau pathology, wherein the targeting ligand is conjugated to a liposome comprising an imaging agent, and imaging at least a portion of the subject to determine if that portion of the subject exhibits tau pathology.

In some aspects, a method for imaging tau pathology in a subject is provided, the method comprising: (i) administering to the subject a detectably effective amount of a targeting ligand-liposome conjugate comprising a targeting ligand that specifically binds to a cell surface marker of tau pathology, wherein the targeting ligand is conjugated to a liposome comprising an imaging agent; and (ii) imaging at least a portion of the subject to determine if the portion exhibits tau pathology. The targeting ligand may comprise an aptamer. The targeting ligand may comprise a stabilized aptamer. The targeting ligand may comprise a thioaptamer. The targeting ligand may comprise a DNA nucleotide sequence selected from the group consisting of Tau_1 (SEQ ID NO: 5; DONGYBM), Tau_3 (SEQ ID NO: 6; MUSQD), Tau_9 (SEQ ID NO: 7), Tau_11 (SEQ ID NO: 8), Tau_10 (SEQ ID NO: 9), Tau_13 (SEQ ID NO: 10), Tau_8 (SEQ ID NO: 11), Tau_4 (SEQ ID NO: 12), Tau_17 (SEQ ID NO: 13), Tau_5 (SEQ ID NO: 14), Tau_21 (SEQ ID NO: 15), Tau_25 (SEQ ID NO: 16), Tau_7 (SEQ ID NO: 17), Tau_31 (SEQ ID NO: 18), Tau_42 (SEQ ID NO: 19), Tau_14 (SEQ ID NO: 20), Tau_19 (SEQ ID NO: 21), Tau_15 (SEQ ID NO: 22), Tau_56 (SEQ ID NO: 23), Tau_34 (SEQ ID NO: 24), Tau_23 (SEQ ID NO: 25), Tau_99 (SEQ ID NO: 26), and Tau_102 (SEQ ID NO: 27). The portion may include a portion of the subject's brain. The imaging may indicate a level of tau pathology sufficient to diagnose the subject as having early stage Alzheimer's disease. The imaging agent may be an MRI contrast enhancing agent, and the level of binding may be determined using MRI. The cell surface marker of tau pathology may comprise a protein selected from KRT6A, KRT6B, HSP, and VIM. The liposome may comprise a membrane, the membrane comprising: a first phospholipid; a sterically bulky excipient that is capable of stabilizing the liposome; a second phospholipid that is derivatized with a first polymer; a third phospholipid that is derivatized with a second polymer, the second polymer being conjugated to the targeting ligand; and the imaging agent, which is encapsulated by or bound to the membrane.

In some aspects, a method for detecting tau pathology is provided, the method comprising: contacting a biological sample with an effective amount of a targeting ligand-liposome conjugate comprising a targeting ligand that specifically binds to a cell surface marker of tau pathology, wherein the targeting ligand is conjugated to a liposome comprising a detectable label; washing the biological sample to remove unbound targeting ligand liposome conjugate; and detecting tau pathology in the biological sample by determining the amount of detectable label remaining in the biological sample. The biological sample may comprise neural cells. The targeting ligand may comprise an aptamer. The targeting ligand may comprise a stabilized aptamer. The targeting ligand may comprise a thioaptamer. The targeting ligand may comprise a DNA nucleotide sequence selected from the group consisting of Tau_1 (SEQ ID NO: 5; DONGYBM), Tau_3 (SEQ ID NO: 6; MUSQD), Tau_9 (SEQ ID NO: 7), Tau_11 (SEQ ID NO: 8), Tau_10 (SEQ ID NO: 9), Tau_13 (SEQ ID NO: 10), Tau_8 (SEQ ID NO: 11), Tau_4 (SEQ ID NO: 12), Tau_17 (SEQ ID NO: 13), Tau_5 (SEQ ID NO: 14), Tau_21 (SEQ ID NO: 15), Tau_25 (SEQ ID NO: 16), Tau_7 (SEQ ID NO: 17), Tau_31 (SEQ ID NO:

18), Tau_42 (SEQ ID NO: 19), Tau_14 (SEQ ID NO: 20), Tau_19 (SEQ ID NO: 21), Tau_15 (SEQ ID NO: 22), Tau_56 (SEQ ID NO: 23), Tau_34 (SEQ ID NO: 24), Tau_23 (SEQ ID NO: 25), Tau_99 (SEQ ID NO: 26), and Tau_102 (SEQ ID NO: 27). The method may further comprise the step of obtaining the biological sample from a subject.

The term "subject" refers to an animal such as a vertebrate or invertebrate animal. In some aspects, the subject is a mammal, including, but not limited to, primates, including simians and humans, equines (e.g., horses), canines (e.g., dogs), felines, various domesticated livestock (e.g., ungulates, such as swine, pigs, goats, sheep, and the like), as well as domesticated pets and animals maintained in zoos. In some aspects, the subject is a human subject. In some aspects, the subject is a subject having an increased risk of developing AD. Risk factors for Alzheimer's disease include genetic predisposition, smoking, diabetes, a history of head injuries, depression, and hypertension. See Burns A, Iliffe S., BMJ., 338: b158 (2009)

The targeting ligand-liposome conjugate can include any of the features described herein. For example, in some aspects, the targeting ligand is an aptamer or stabilized aptamer, while in further aspects, the targeting ligand is a thioaptamer. In yet further aspects, the aptamer or stabilized aptamer used in the method comprises a DNA nucleotide sequence selected from, including selected from the group consisting of Tau_1 (SEQ ID NO: 5; DONGYBM), Tau_3 (SEQ ID NO: 6; MUSQD), Tau_9 (SEQ ID NO: 7), Tau_11 (SEQ ID NO: 8), Tau_10 (SEQ ID NO: 9), Tau_13 (SEQ ID NO: 10), Tau_8 (SEQ ID NO: 11), Tau_4 (SEQ ID NO: 12), Tau_17 (SEQ ID NO: 13), Tau_5 (SEQ ID NO: 14), Tau_21 (SEQ ID NO: 15), Tau_25 (SEQ ID NO: 16), Tau_7 (SEQ ID NO: 17), Tau_31 (SEQ ID NO: 18), Tau_42 (SEQ ID NO: 19), Tau_14 (SEQ ID NO: 20), Tau_19 (SEQ ID NO: 21), Tau_15 (SEQ ID NO: 22), Tau_56 (SEQ ID NO: 23), Tau_34 (SEQ ID NO: 24), Tau_23 (SEQ ID NO: 25), Tau_99 (SEQ ID NO: 26), and Tau_102 (SEQ ID NO: 27).

In some aspects, a method is provided for generating an image of a tissue region of a subject, by administering to the subject a detectably effective amount of the composition for detecting tau pathology, and generating an image of a portion of the subject (i.e., a tissue region) to which the composition including the imaging agent has distributed. To generate an image of the tissue region, it is necessary for a detectably effective amount of imaging agent to reach the tissue region of interest, but it is not necessary that the imaging agent be localized in this region alone. However, in some aspects, the compositions including the imaging agents are targeted or administered locally such that they are present primarily in the tissue region of interest. Examples of images include two-dimensional cross-sectional views and three-dimensional images. In some aspects, a computer is used to analyze the data generated by the imaging agents to generate a visual image. The tissue region or portion of the subject can be an organ of a subject such as the brain, heart, lungs, or blood vessels. In other aspects, the portion of the subject can be a tissue region known to include neural cells, such as the brain. Examples of imaging methods include optical imaging, fluorescence imaging, computed tomography, positron emission tomography, single photon emission computed tomography, and MRI. Any other suitable type of imaging methodology known by those skilled in the art is contemplated.

In some aspects, the imaging agent is an MRI contrast enhancing agent, and the level of binding is determined using MRI. MRI is a medical application of nuclear magnetic resonance and forms pictures of the anatomy and physiological processes of the body using strong magnetic fields, magnetic field gradients, and radio waves to generate images of a portion of a subject. MRI is commonly used for neuroimaging, cardiovascular imaging, musculoskeletal imaging, liver imaging, and gastrointestinal imaging. MRI for imaging of anatomical structures or blood flow does not require contrast agents as the varying properties of the tissues or blood provide natural contrasts. However, for more specific types of imaging, exogenous contrast agents may be administered. For a review of neural imaging techniques, see Mehrabian et al. (Front Oncol., 9:440 (2019).

In another aspect, a method is provided for detecting tau pathology. The method includes contacting a biological sample with an effective amount of a targeting ligand-liposome conjugate comprising a targeting ligand that specifically binds to a cell surface marker of tau pathology, wherein the targeting ligand is conjugated to a liposome comprising a detectable label, washing the biological sample to remove unbound targeting ligand liposome conjugate, and detecting tau pathology in the biological sample by determining the amount of detectable label remaining in the biological sample.

The targeting ligand-liposome conjugate can include any of the features described herein. For example, in some aspects, the targeting ligand is an aptamer or stabilized aptamer, while in further aspects, the targeting ligand is a thioaptamer. In yet further aspects, the aptamer or stabilized aptamer used in the method comprises a DNA nucleotide sequence selected from, including selected from the group consisting of Tau_1 (SEQ ID NO: 5; DONGYBM), Tau_3 (SEQ ID NO: 6; MUSQD), Tau_9 (SEQ ID NO: 7), Tau_11 (SEQ ID NO: 8), Tau_10 (SEQ ID NO: 9), Tau_13 (SEQ ID NO: 10), Tau_8 (SEQ ID NO: 11), Tau_4 (SEQ ID NO: 12), Tau_17 (SEQ ID NO: 13), Tau_5 (SEQ ID NO: 14), Tau_21 (SEQ ID NO: 15), Tau_25 (SEQ ID NO: 16), Tau_7 (SEQ ID NO: 17), Tau_31 (SEQ ID NO: 18), Tau_42 (SEQ ID NO: 19), Tau_14 (SEQ ID NO: 20), Tau_19 (SEQ ID NO: 21), Tau_15 (SEQ ID NO: 22), Tau_56 (SEQ ID NO: 23), Tau_34 (SEQ ID NO: 24), Tau_23 (SEQ ID NO: 25), Tau_99 (SEQ ID NO: 26), and Tau_102 (SEQ ID NO: 27).

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers, and the like. Similarly, enzymatic labels may be detected by providing the appropriate substrates for the enzyme and detecting the resulting reaction product. The level of detected label can be compared to control levels to determine if the biological sample exhibits an increased level of cell surface markers for tau pathology.

Biological samples can be mammalian body fluids, sera such as blood (including whole blood, as well as its plasma and serum), CSF (spinal fluid), urine, sweat, saliva, tears, pulmonary secretions, breast aspirate, prostate fluid, seminal fluid, stool, cervical scraping, cysts, amniotic fluid, intraocular fluid, mucous, moisture in breath, animal tissue, cell lysates, tumor tissue, hair, skin, buccal scrapings, nails, bone marrow, cartilage, prions, bone powder, ear wax, etc., or even from external or archived sources such as tumor samples (i.e., fresh, frozen, or paraffin-embedded). Samples, such as body fluids or sera, obtained during the course of clinical trials may be suitable. In some aspects, the biological sample comprises CSF or a sample containing neural cells, such as a neural (e.g., brain) tissue sample.

A biological sample may be fresh or stored. Samples can be stored for varying amounts of time, such as being stored for an hour, a day, a week, a month, or more than a month. The biological sample may be expressly obtained for use or may be a sample obtained for another purpose that can be subsampled. In some aspects, it may be useful to filter, centrifuge, or otherwise pre-treat the biological sample to remove impurities or other undesirable matter that could interfere with analysis of the biological sample.

In some aspects, the method includes the step of obtaining the biological sample from a subject. The method of obtaining the biological sample will vary depending on the type of biological sample being obtained, and such methods are well-known to those skilled in the art. For example, a sample of brain tissue can be obtained using a sterotactic brain needle biopsy, while a sample of cerebrospinal fluid can be obtained via a lumbar puncture.

ADx-002 Nanoparticles for MRI

Figure 4A:
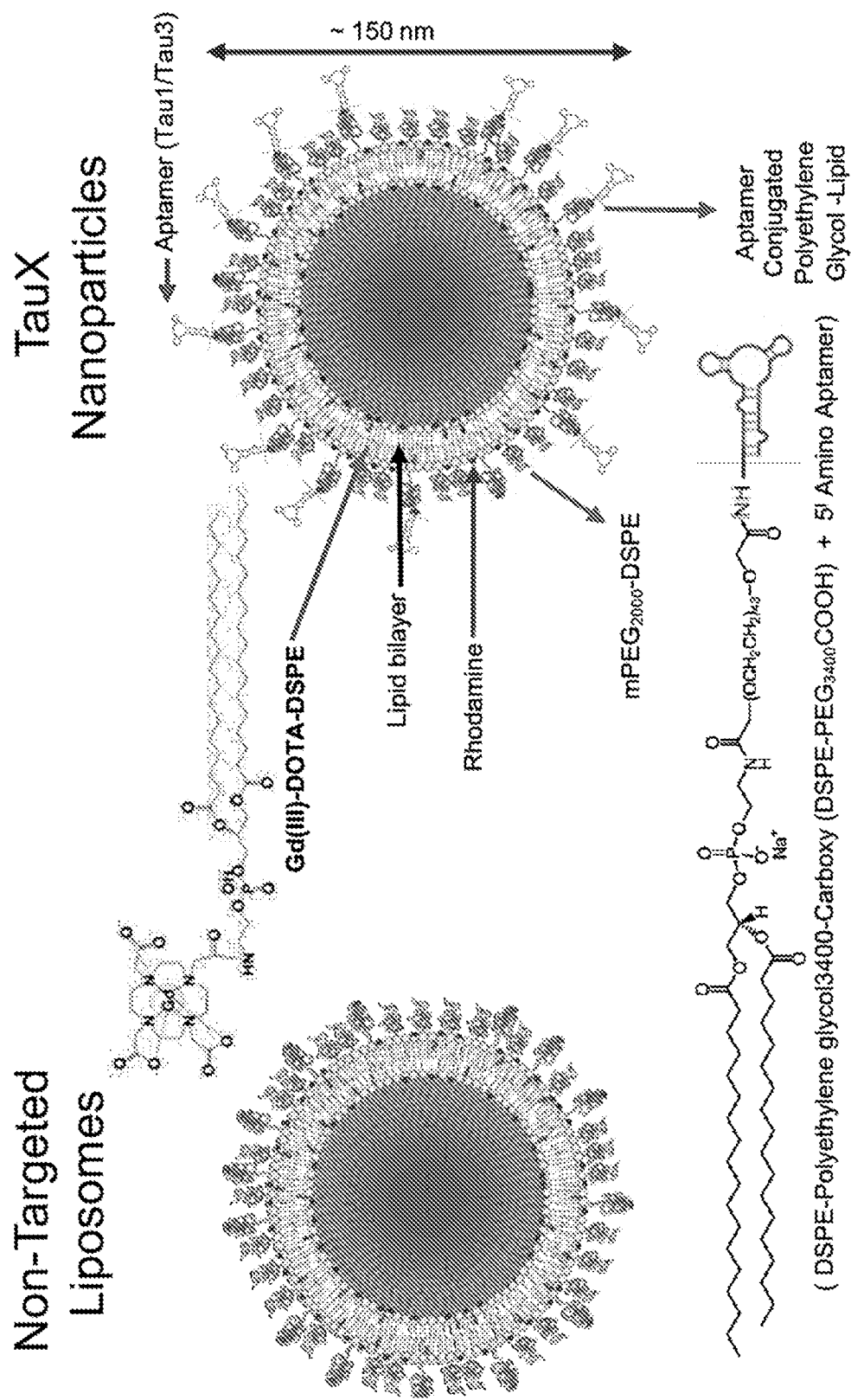
FIG. 4A shows an example liposomal-Gd nanoparticle contrast agent. As shown, the liposomal bilayer incorporates DSPE-DOTA-Gd for MR contrast, lissamine rhodamine for fluorescence imaging, DSPEmPEG2000 to enhance circulation half-life, DSPEPEG3400 for non-targeted (control/stealth) liposomes, and DSPE-PEG3400-aptamer (Tau_1 (SEQ ID NO: 5; DONGYBM) or Tau_3 (SEQ ID NO: 6; MUSQD)) for targeted ADx-002 (or "TauX") nanoparticles.

For in vivo imaging of the hyperphosphorylative state in the brain of live mice, two types of aptamer-targeted nanoparticles were developed as molecular MRI contrast agents (ADx-002). One displayed the Tau_1 (SEQ ID NO: 5; DONGYBM) aptamer and the other displayed the Tau_3 (SEQ ID NO: 6; MUSQD) aptamer. PEGylated liposomal nanoparticles were synthesized using a lipid mixture that included lipid-tethered Gd-DOTA for MR imaging and cholesterol for liposomal stability. Lipidized rhodamine was also included for studying ex-vivo microscopic distribution of liposomal nanoparticles in brain tissues using fluorescence microscopy. The ADx-002 compositions also included DSPE-mPEG2000 to increase the in vivo circulation time. Particles had a hydrodynamic diameter of ~ 150 nm, ~86,000 Gd-chelates per liposome, and ~500 aptamers conjugated to the outer leaflet of each liposomal nanoparticle (FIG. 4A).

In Vivo Molecular MRI Using ADx-002 for Detection of Hyperphosphorylative Cells

Figure 5A:
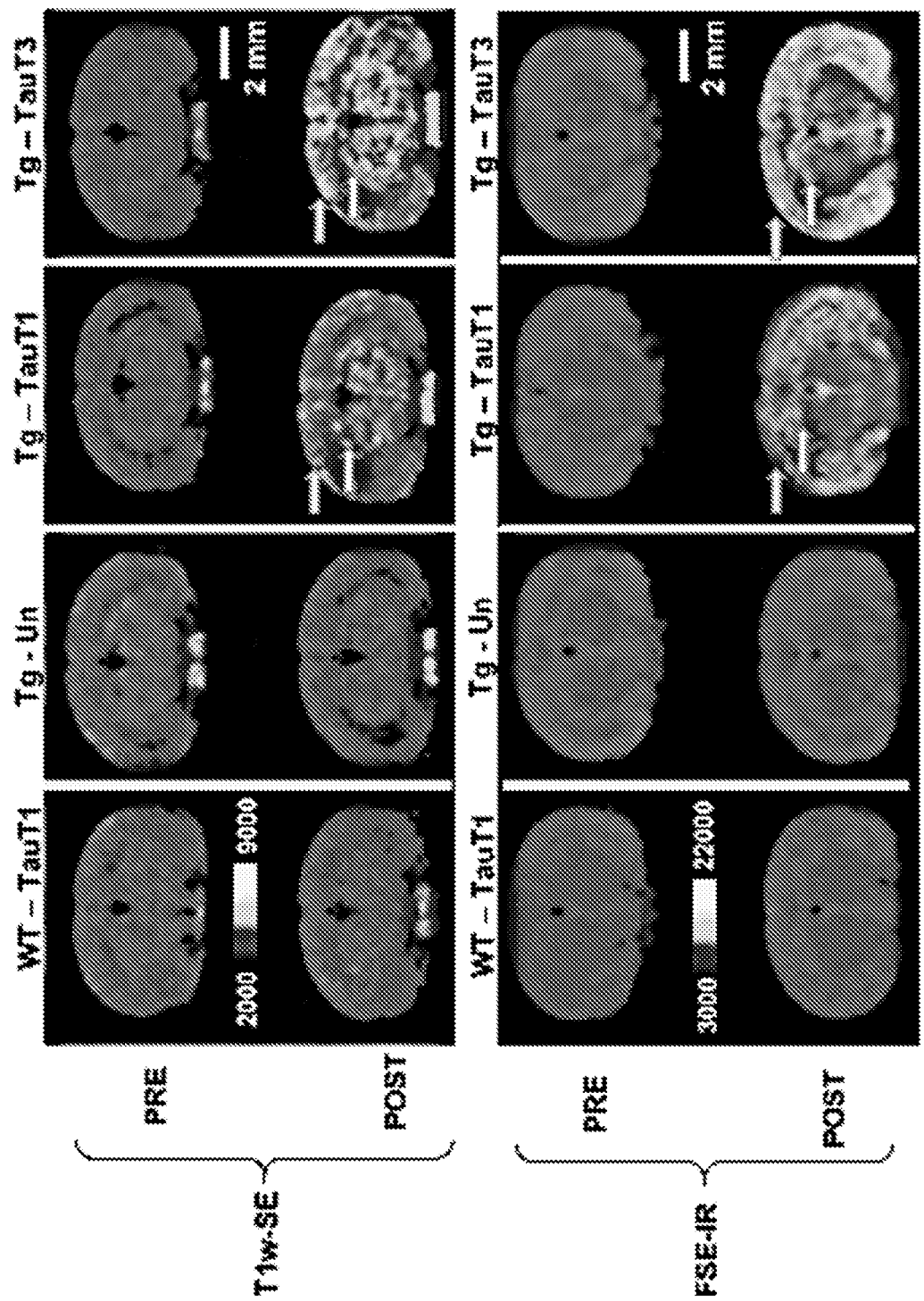
FIG. 5A shows pre- and post-contrast images for T1-weighted spin echo (T1w-SE) and fast spin echo inversion recovery (FSE-IR), which demonstrate signal enhancement in delayed post-contrast scans of transgenic (Tg) P301S mice treated with ADx-002 relative to age-matched wild type (WT) controls. The Tg animals showed high enhancement in cortical and hippocampal regions (as indicated by the arrows). The Tg animals show no signal enhancement four days after injection of untargeted contrast (UC).
Figure 5B:
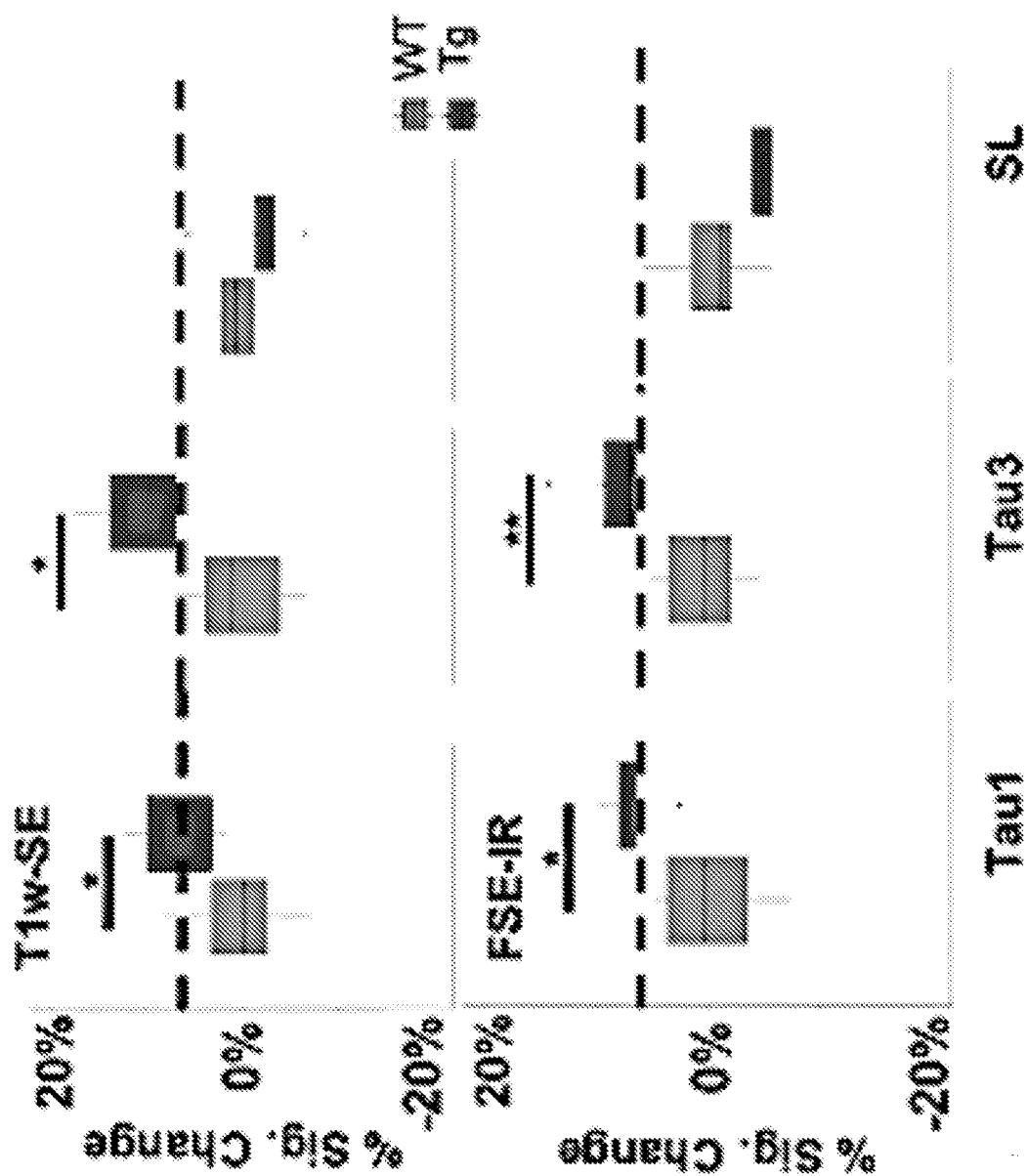
FIG. 5B shows box and whisker plots demonstrating signal enhancement in Tg animals relative to WT counterparts and UC-treated Tg animals for both T1w-SE and FSE-IR sequences (*p<0.05; **p<0.005). The dotted line indicates the signal threshold for determining sensitivity (two standard deviations above baseline noise, ~6%).

Studies were performed in P301S transgenic and age-matched wild type mice at 2-3 months of age. At this age, transgenic animals do not show frank tau pathology (i.e., neurofibrillary tangles), but practically all will develop tau pathology by around 8 months of age. Animals underwent baseline, pre-contrast MRI. Thereafter, animals were intravenously administered MRI contrast agent (ADx-002-Tau_1 (SEQ ID NO: 5; DONGYBM) or ADx-002-Tau_3 (SEQ ID NO: 6; MUSQD) or non-targeted control stealth liposomes. Delayed post-contrast MRI was performed 4 days later. MR images were acquired using a T1w-SE sequence and an FSE-IR sequence. Tg mice administered ADx-002-Tau_1 (SEQ ID NO: 5; DONGYBM) or ADx-002-Tau_3 (SEQ ID NO: 6; MUSQD) demonstrated signal enhancement in the cortex and the hippocampus regions of the brain (FIG. 5A). WT mice administered ADx-002-Tau_1 (SEQ ID NO: 5; DONGYBM) or ADx-002-Tau_3 (SEQ ID NO: 6; MUSQD) did not show signal enhancement in the brain. Similarly, Tg mice administered non-targeted liposomal-Gd contrast agent did not show signal enhancement in cortex or hippocampus. These regions of interest were further analyzed quantitatively, and signal-enhancement between the Tg and WT mice were found to be statistically significant (p <0.05) (FIG. 5B).

Figure 5C:
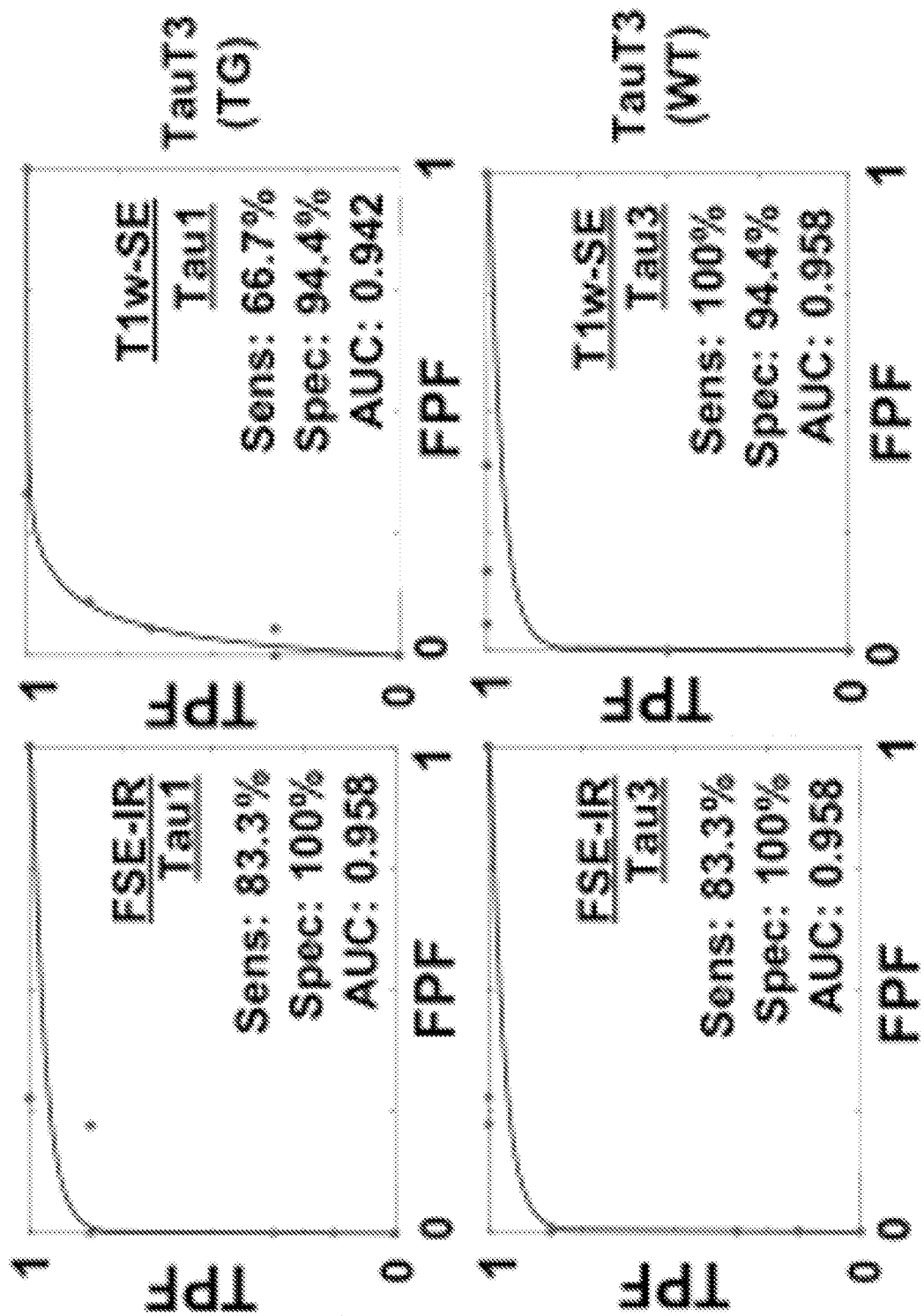
FIG. 5C shows Receiver operating characteristic (ROC) curves plotting true positive fraction (TPF) against false positive fraction (FPF), demonstrating ADx-002 accuracy in identifying early age Tg animals. A fitted curve connects the observed operating points. Area under curve (AUC) is calculated using the fitted curve, and sensitivity (true positive rate) and specificity (true negative rate) for both formulations are listed.

A baseline enhancement threshold of ~6% (=2× standard deviation of signal in baseline scans) was used as the classification threshold. Animals that showed signal enhancement above the threshold were identified as positives. ROC curves were generated with a six-point ordinal scale to assess sensitivity and specificity for detecting the genotype, using ADx-002-Tau_1 (SEQ ID NO: 5; DONGYBM) or ADx-002-Tau_3 (SEQ ID NO: 6; MUSQD) contrast agents, and constructed over the entire tested group, including controls. The aptamer-targeted nanoparticle contrast agents, ADx-002-Tau_1 (SEQ ID NO: 5; DONGYBM) andr ADx-002-Tau_3 (SEQ ID NO: 6; MUSQD), showed overall AUC and accuracy of ~0.95. ADx-002-Tau_3 (SEQ ID NO: 6; MUSQD) demonstrated higher sensitivity than ADx-002-Tau_1 (SEQ ID NO: 5; DONGYBM) (FIG. 5C).

Figure 5D:
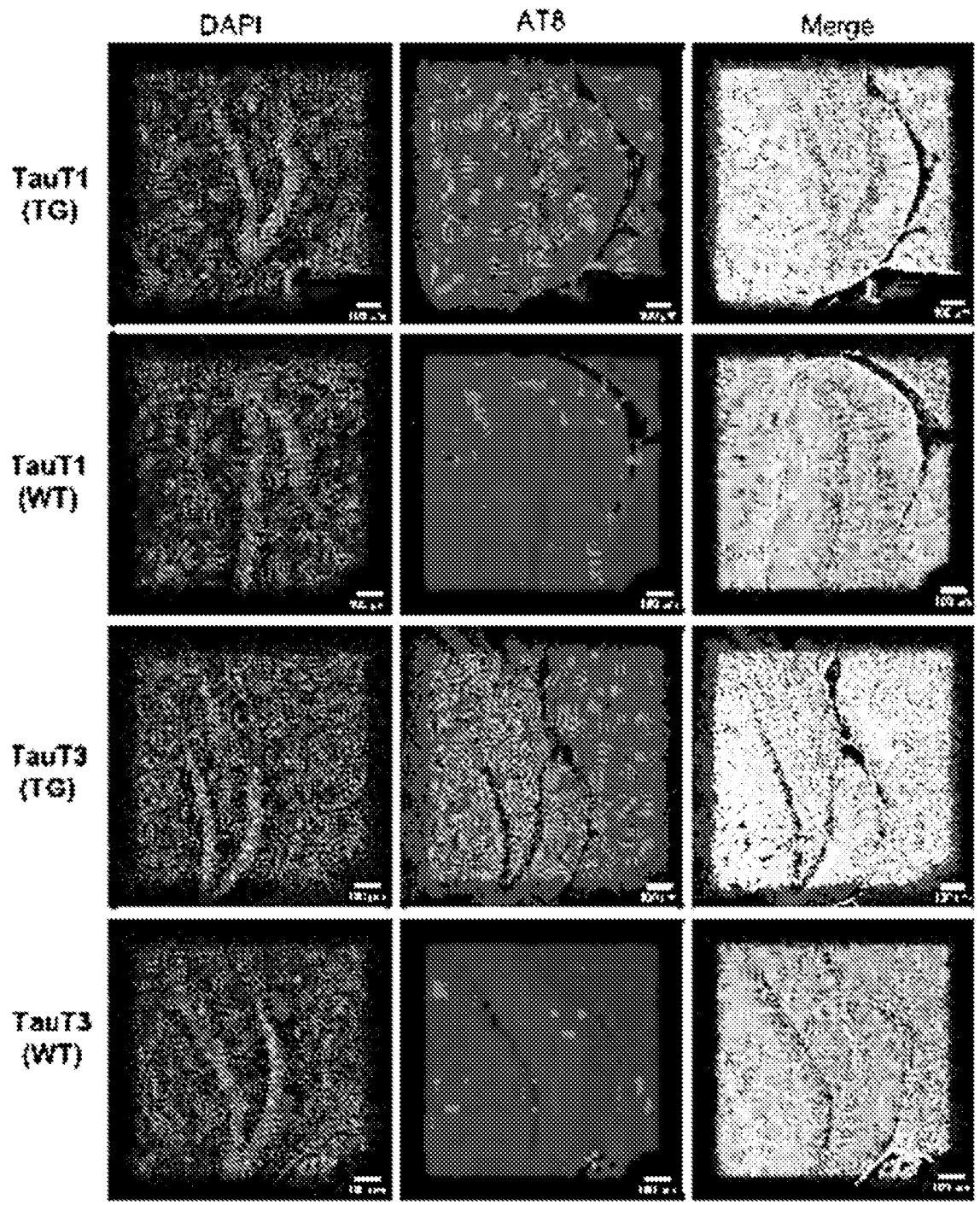
FIG. 5D shows the results of immunofluorescence studies on brain sections harvested post MRI scans of P301S mice treated with ADx-002 nanoparticles.

Post-mortem brain analysis was performed in 2-3 month old transgenic and wild-type mice. Immunofluorescence analysis using AT8 antibody staining revealed the presence of hyperphosphorylated tau species in transgenic mice but not in wild type mice (FIG. 5D). A 100% concordance was observed between AT8 positivity and animal genotype. In summary, in vivo studies demonstrated that ADx-002 enabled in vivo molecular MRI of the hyperphosphorylative state months before frank tau pathology, i.e., the presence of neurofibrillary tangles, becomes evident in Tg mice.

Target Identification of Aptamers

Figure 6A:
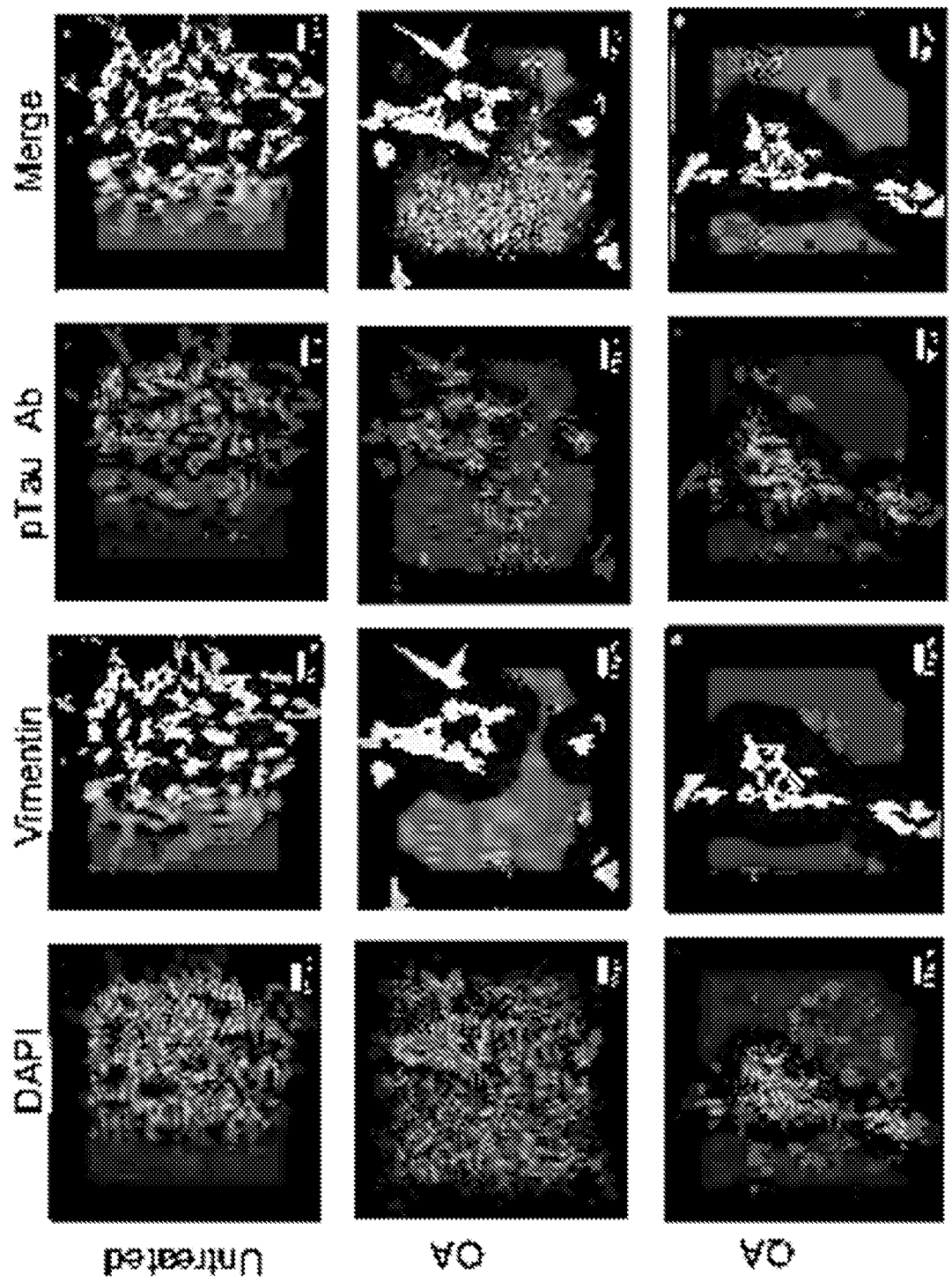
FIG. 6A shows the presence of the thioaptamers binding a target on SHSY5Y cells; undifferentiated and hyperphosphorylated OA (24 h, 30 nM) and QA (24 h, 100 nM) were co-stained with VIM (D21H3) and ptau (AT100) antibodies.
Figure 6B:
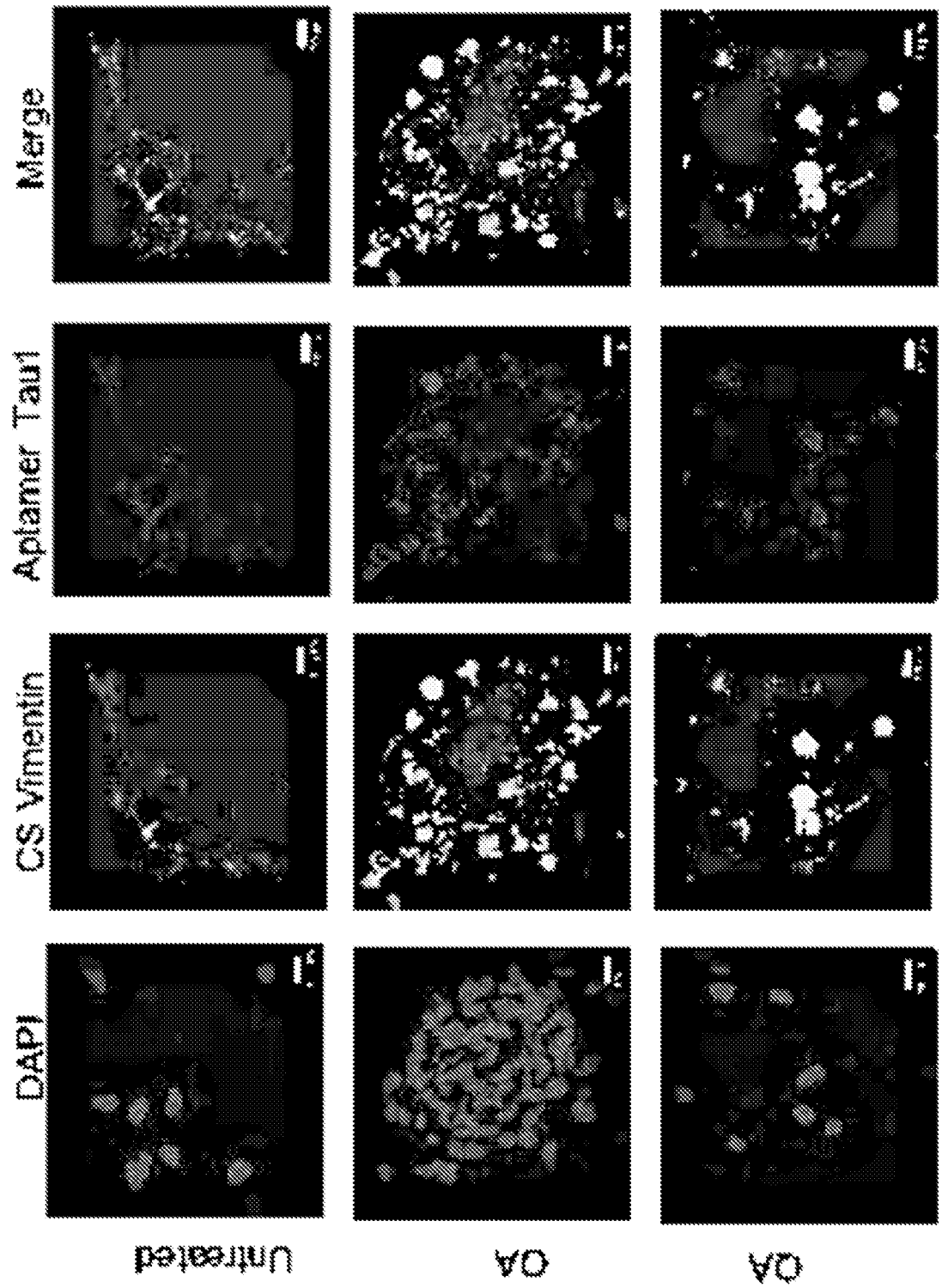
FIG. 6B shows the presence of the aptamers binding target on SHSY5Y cells; undifferentiated and hyperphosphorylated OA (24 h, 30 nM) and QA (24 h, 100 nM) co-stained with cell surface (CS) VIM (Clone 84-1) antibody and aptamer Tau_1 (SEQ ID NO: 5; DONGYBM (50 nM); nuclei were counterstained with DAPI.
Figure 6C:
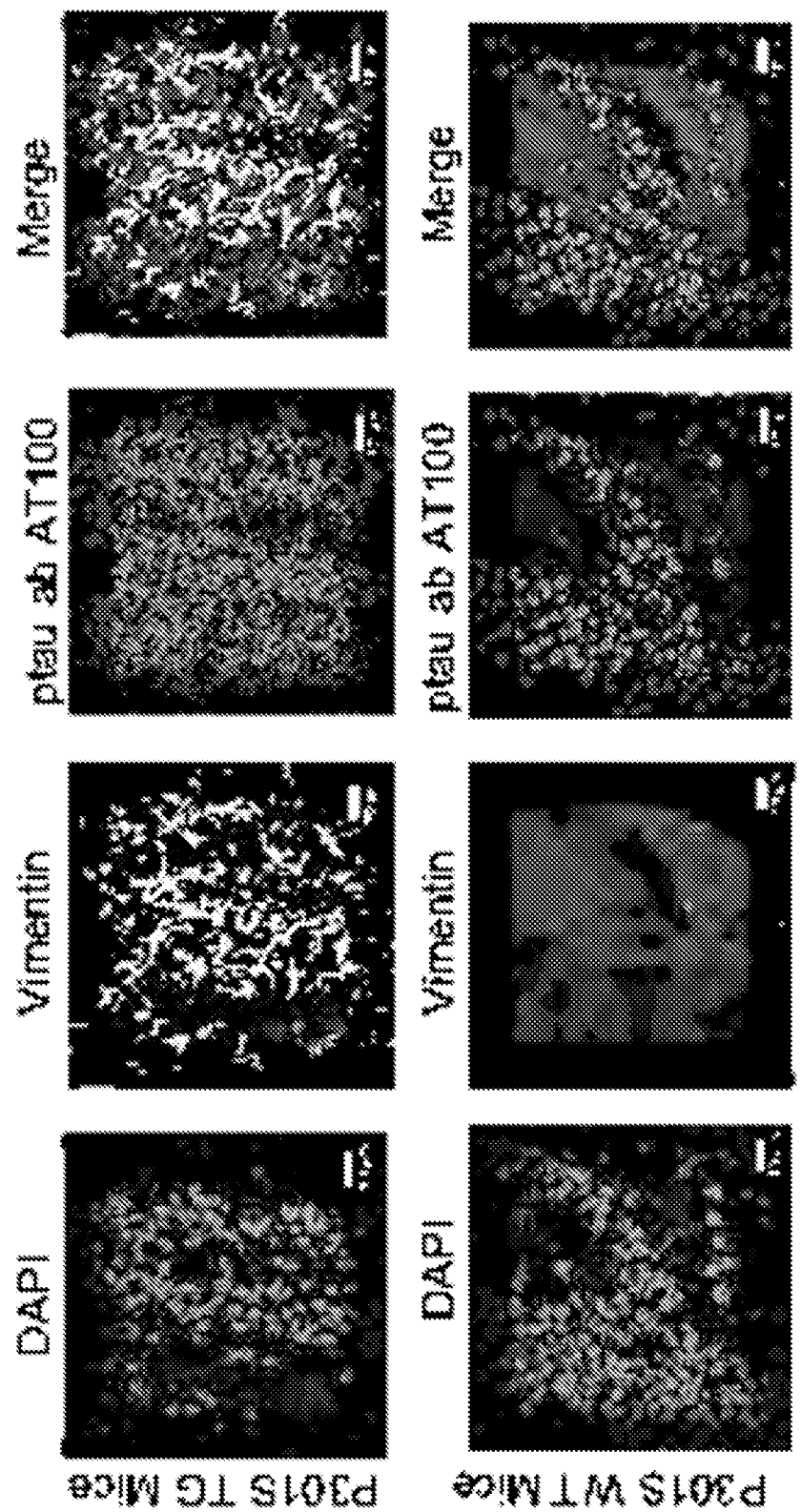
FIG. 6C shows expression of VIM in P301STG and WT frozen mouse tissue sections stained with VIM (SP20) and ptau (AT100) antibodies and DAPI stained nuclei.

To characterize the binding target of the aptamers, an aptamer-based pulldown assay was performed, along with aptamer-based immunoprecipitation, followed by mass-spectrometry. The assay was performed for both Tau_1 (SEQ ID NO: 5; DONGYBM) and Tau_3 (SEQ ID NO: 6; MUSQD) aptamers. A ranking of the abundance scores for identified proteins revealed keratin 6a, Keratin 6b, and VIM as possible binding targets. The surface expression of Keratin 6a, 6b was similar on wild-type and transgenic tissue sections, whereas the VIM expression was higher in the Tg mice (FIG. 6C). SH-SY5Y cells under undifferentiated and differentiated hyperphosphorylative conditions show increasing levels of VIM (FIGS. 6A, 6B), further suggesting it is a potential target of aptamers Tau_1 (SEQ ID NO: 5; DONGYBM) and Tau_3 (SEQ ID NO: 6; MUSQD) specific to the hyperphosphorylated state.

VIM Targeted WNP for MRI

Figure 4B:
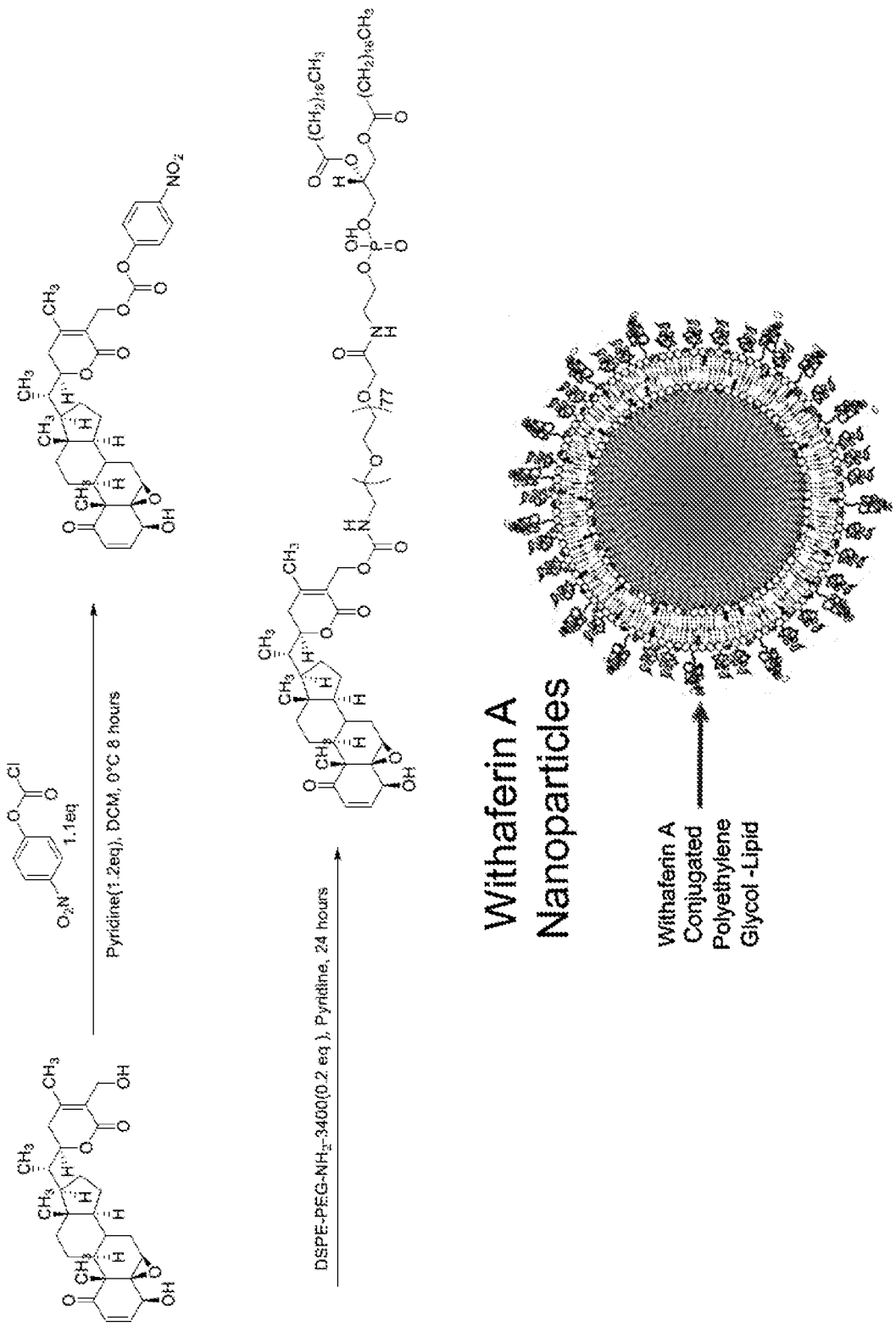
FIG. 4B shows the synthesis of lipidized Withaferin A (WNP).
Figure 7:
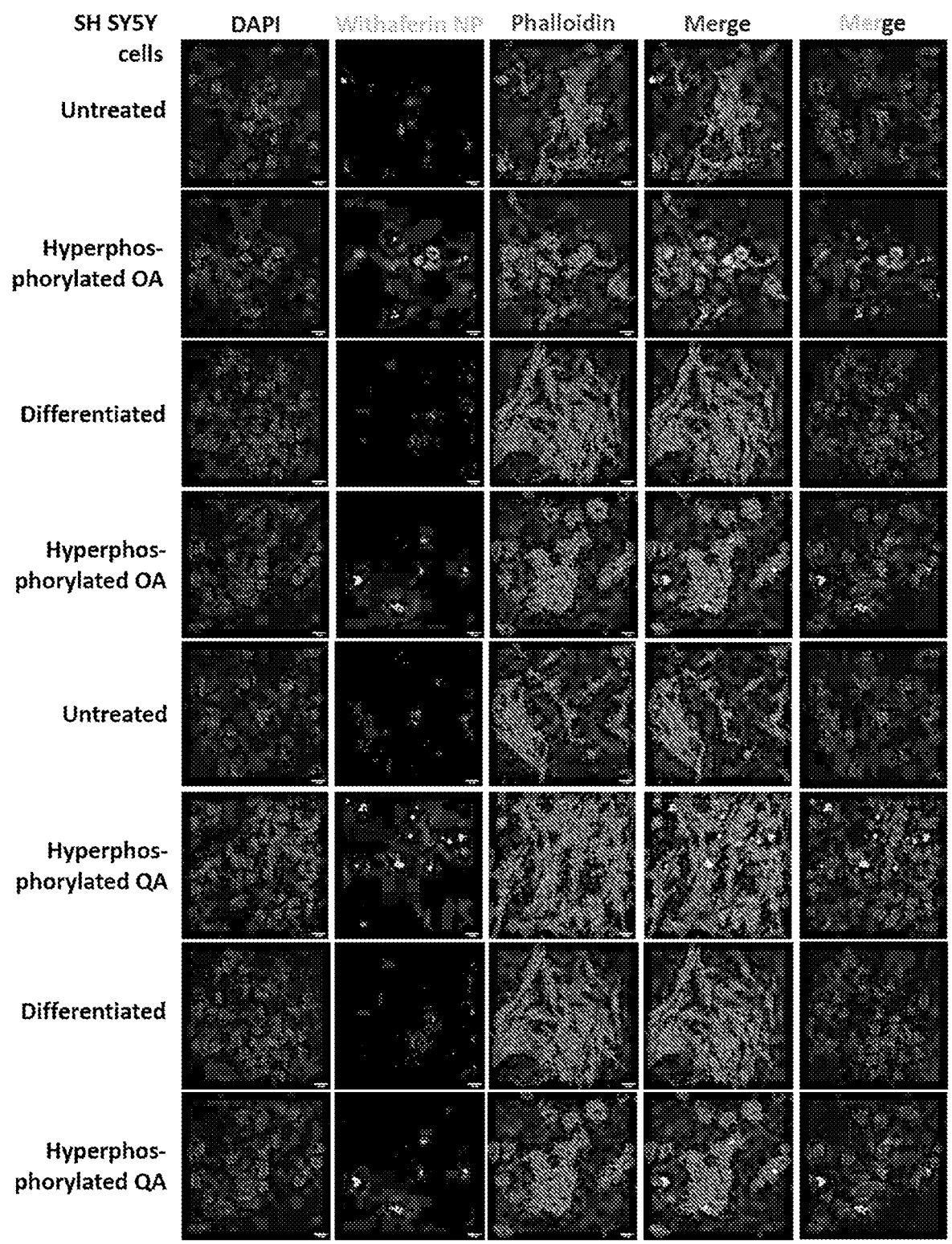
FIG. 7 shows the results of an in vitro binding study of Withaferin nanoparticles. Differentiated and hyperphosphorylative SH SY5Y cells were incubated with Rhodamine labeled Withaferin nanoparticles (WNP) for 30 min at 37° C. Binding is specificity observed to cells under hyperphosphorylative conditions.

Liposomal nanoparticles targeting VIM were prepared using Withaferin A, a small molecule that binds the conserved cysteine 382 residue on tetrameric VIM in a binding pocket that includes Gln 324 and Asp 331. DSPE-PEG3400-Withaferin A was synthesized and use do substitute for the carboxy PEG in the aptamer targeted ADx-002 formulation to yield WNP with ~600 Withaferin A molecules per liposomal nanoparticle (FIG. 4B). Specific binding of WNPs to neuronally differentiated SH-SY5Y cells under hyperphosphorylative conditions is shown in FIG. 7.

Figure 8A:
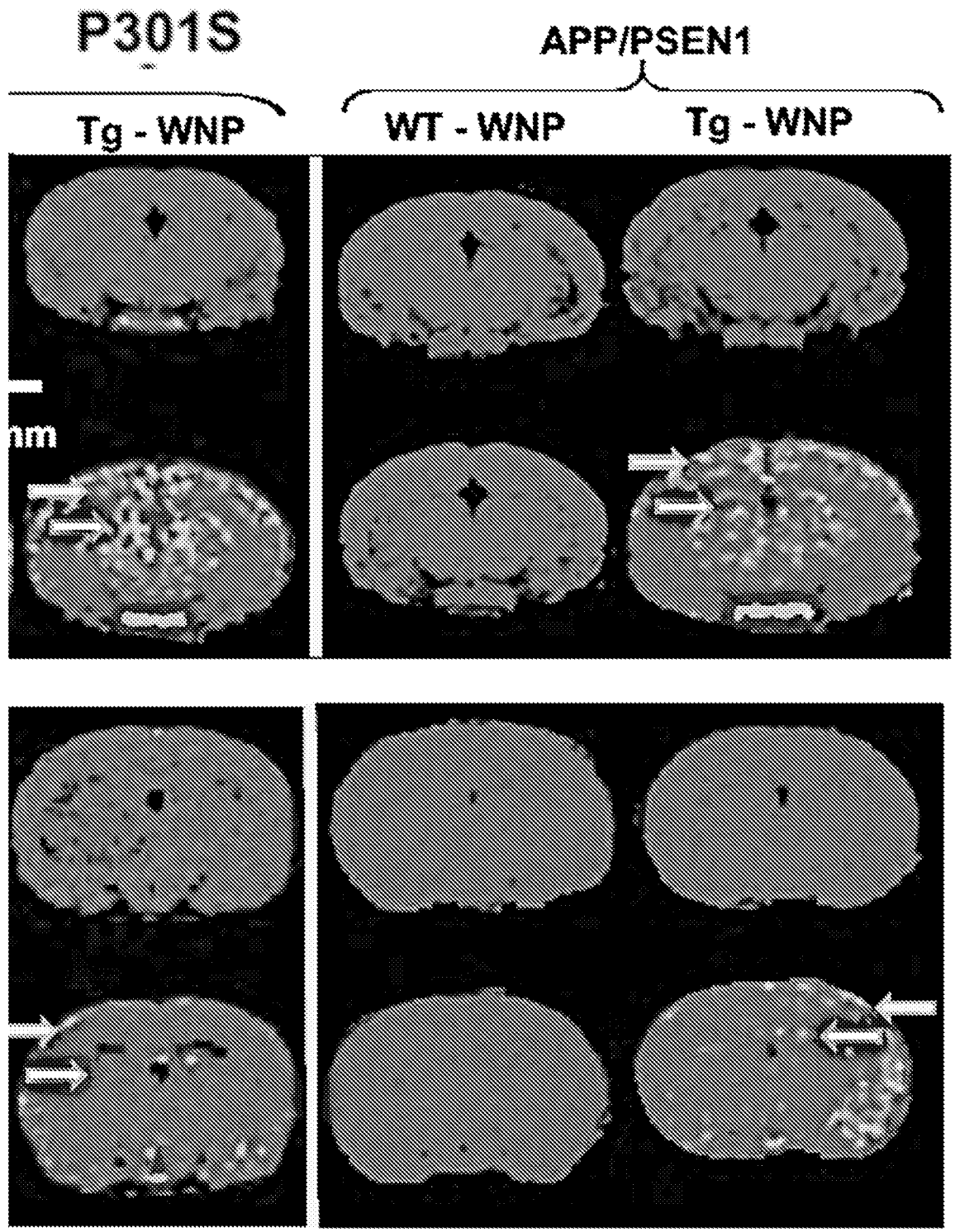
FIG. 8A shows pre- and post-contrast MRI images for T1-weighted spin echo (T1w-SE) and fast spin echo inversion recovery (FSE-IR), demonstrating signal enhancement in delayed post-contrast scans of Tg P301S mice and APP/PSEN1 mice treated with WNP relative to age-matched WT controls.
Figure 8B:
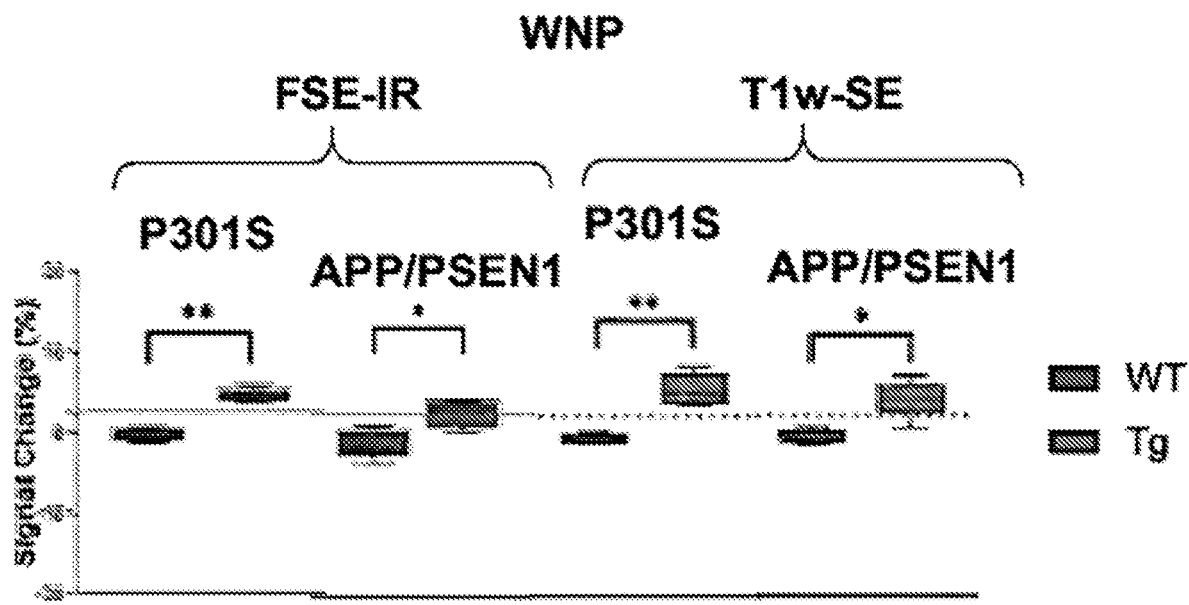
FIG. 8B shows box and whisker plots demonstrating signal enhancement in Tg P301S mice and APP/PSEN1 mice treated with WNP relative to WT counterparts and UC-treated Tg animals for both T1w-SE and FSE-IR sequences. The dotted line indicates the signal threshold for determining sensitivity (two standard deviations above baseline noise, ~6%).
Figure 8C:
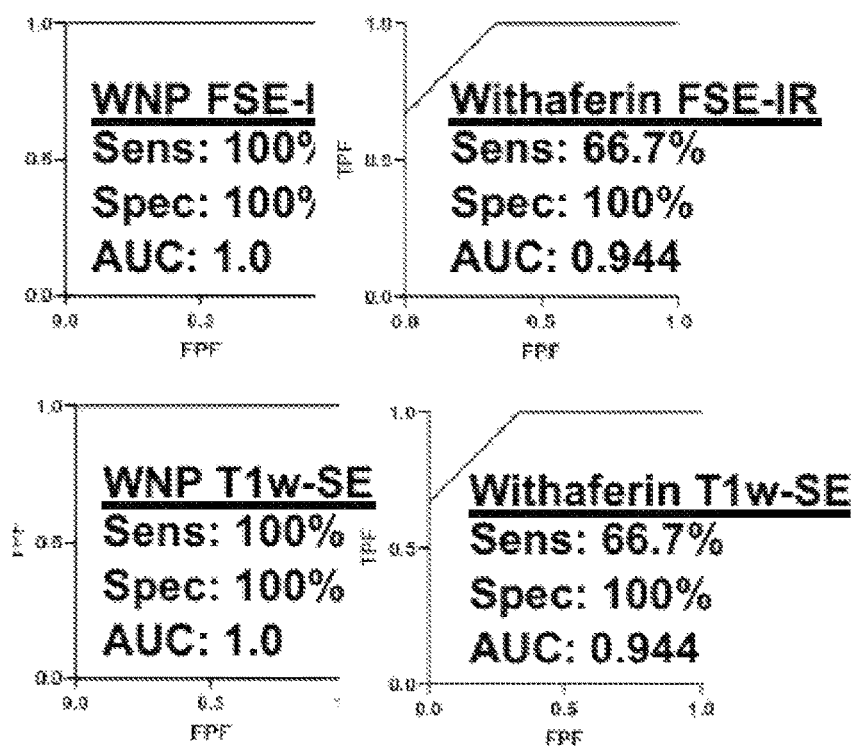
FIG. 8C shows ROC curves plotting true positive TPF against FPF, demonstrating WNP accuracy in identifying early age Tg animals. A fitted curve connects the observed operating points. AUC is calculated using the fitted curve, and sensitivity (true positive rate) and specificity (true negative rate) are listed.
Figure 9:
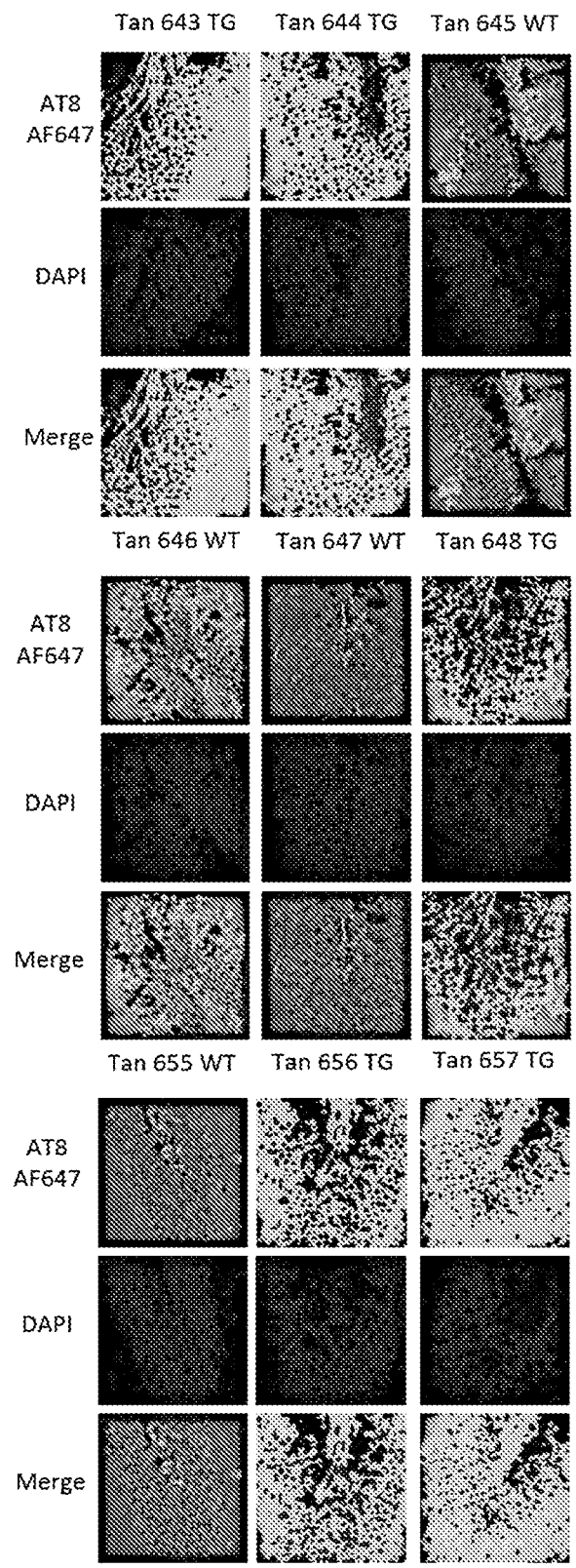
FIG. 9 shows the phosphorylation status of tau in WNP treated P301S mice. P301S mice aged 2 months treated with WNP were sacrificed immediately after MR image acquisition, and intact brains were recovered for immunofluorescence. Frozen brain tissue sections were stained with AT8 antibody. Positive signal on Tg mice sections but not on the WT confirm the presence of phosphorylated tau in Tg mice.

Two month old P301S mice and APP/PSEN1 were injected with WNP and imaged using the same T1-weighted sequences as used with the ADx-002 nanoparticles. No signal enhancement was observed in the WT mice models, whereas the Tg mice (P301S and APP/PSEN1) showed distinct signal enhancement in the cortex and hippocampus regions and were identified as positives (FIGS. 8A and 8B). Group statistical analysis (FIGS. 8B and 8C) revealed that the VIM-targeted WNP contrast agents showed overall AUC and accuracy of ~1.00. The phosphorylation status of tau in transgenic mice was confirmed by immunofluorescence (FIG. 9).

Alzheimer's Disease

In some aspects, the imaging indicates a level of tau pathology sufficient to diagnose the subject as having AD. In further aspects, the method indicates that the subject has early stage AD, an increased risk of developing AD, or both. A level of tau pathology sufficient to diagnose the subject as having AD or early stage AD can be due to the presence of increased levels of cell surface markers reflecting an increased level of tau phosphorylation (e.g., hyperphosphorylation) within the cell (e.g., a neural cell). Examples of cell surface markers reflecting an increased level of tau phosphorylation include KRT6A, KRT6B, HSP, and VIM.

AD is a chronic neurodegenerative disease that usually starts slowly, gradually worsens over time, and is the cause of 60-70% of cases of dementia. AD is characterized by loss of neurons and synapses in the cerebral cortex and certain subcortical regions. This loss results in gross atrophy of the affected regions, including degeneration in the temporal lobe, parietal lobe, and parts of the frontal cortex and cingulate gyrus. AD is a protein misfolding disease (proteopathy) caused by plaque accumulation of abnormally folded amyloid beta protein and tau protein in the brain.

Diagnosis of AD is most often made in the moderate stage. Typically, the symptoms of AD are cognitive dysfunction or deficiency and include dementia confirmed by medical and psychological exams, problems in at least two areas of mental functioning, and progressive loss of memory and other mental functions, especially where symptoms began between the ages of 40 and 90, no other disorders account for the dementia, and no other conditions are present that may mimic dementia, including hypothyroidism, overmedication, drug-drug interactions, vitamin B12 deficiency, and depression. As the disease advances, symptoms can include problems with language, disorientation (including easily getting lost), mood swings, loss of motivation, not managing self-care, and behavioral issues. In some aspects, the methods and compositions described herein provide for the detection of early stage AD, which can be present before one or more of these symptoms has manifested. Accordingly, in some aspects, the methods are used to diagnose a subject that does not exhibit any other symptoms of AD.

In some aspects, the methods further comprise providing prophylaxis or treatment of AD to the subject. Prophylaxis of AD includes changes in lifestyle and diet that decrease the risk of developing AD.

Several medicines have also been identified that can be used to treat the cognitive problems associated with AD. These include acetylcholinesterase inhibitors such as tacrine, rivastigmine, galantamine, and donepezil, as well as the NMDA receptor antagonist memantine. Huperzine A is a promising agent for treating AD, and atypical antipsychotics can be used for reducing aggression and psychosis in people having AD.

Pharmaceutical Compositions

In some aspects, the compositions described herein are delivered as a pharmaceutical composition. The pharmaceutical compositions are prepared according to standard techniques and may further comprise a pharmaceutically acceptable carrier. Generally, normal saline will be employed as the pharmaceutically acceptable carrier. Other suitable carriers include, e.g., water, buffered water, isotonic solution (e.g., dextrose), 0.4% saline, 0.3% glycine, and the like, including glycoproteins for enhanced stability, such as albumin, lipoprotein, globulin, and the like. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, and the like, for example, sodium acetate, sodium lactate, sodium chloride, potassium chloride, calcium chloride, and the like. Additionally, the liposome compositions can be suspended in suspensions that include lipid-protective agents that protect lipids against free-radical and lipid-peroxidative damages on storage. Lipophilic free-radical quenchers, such as $\alpha$-tocopherol and water-soluble iron-specific chelators, such as ferrioxamine, are suitable.

The concentration of liposome compositions in the pharmaceutical formulations can vary widely, e.g., from less than about 0.05%, usually at or at least about 2-5%, to as much as 10 to 30% by weight, and will be selected primarily by fluid volumes, viscosities, etc., in accordance with the particular mode of administration selected. For example, the concentration may be increased to lower the fluid load associated with treatment. The amount of compositions administered will depend upon the particular aptamer used, the disease state being treated, and the judgment of the clinician. Generally, the amount of composition administered will be sufficient to deliver a therapeutically effective dose of the nucleic acid. The quantity of composition necessary to deliver a therapeutically effective dose can be determined by one skilled in the art. Typical dosages will generally be between about 0.01 and about 50 mg nucleic acid per kilogram of body weight, between about 0.1 and about 10 mg nucleic acid/kg body weight, or between about 2.0 and about 5.0 mg nucleic acid/kg of body weight. For administration to mice, the dose is typically 50-100 µg per 20 g mouse.

Kits

In some aspects, kits are provided for preparing the liposome complexes/compositions. Such kits can be prepared from readily available materials and reagents, as described above. For example, such kits can comprise any one or more of the following materials: liposomes, nucleic acid (condensed or uncondensed), hydrophilic polymers, hydrophilic polymers derivatized with targeting ligands such as aptamers, and instructions. A wide variety of kits and components can be prepared, depending upon the intended user of the kit and the needs of the user. For example, the kit may contain any one of the targeting moieties for targeting the complex to a specific cell type, as described above.

Instructional materials for preparation and use of the liposome complexes can be included. While the instructional materials typically comprise written or printed materials, they are not limited to such. Any medium capable of storing such instructions and communicating them to an end user is contemplated. Such media include, but are not limited to, electronic storage media (e.g., magnetic discs, tapes, cartridges, chips), optical media (e.g., CD ROM), and the like. Such media may include addresses to internet sites that provide such instructional materials.

In various aspects, the instructions may direct a user to carry out any of the method steps described herein. For example, the instructions may direct a user to diagnose the risk that a subject will develop AD by detecting the presence of tau pathology using the targeted liposomal compositions described herein.

Examples have been included to describe more clearly particular aspects of the invention. However, there are a wide variety of other aspects within the scope of the present invention, which should not be limited to the examples provided herein.

EXAMPLES

Materials and Methods

Cell-lines. SH-SY5Y cells (ATCC, Manassas, VA, #CRL-2266™) were obtained from Dr. Jason Shohet's lab at the Texas Children's Hospital, Houston. Immortalized human hepatocytes (THLE-3) were purchased from American Type Culture Collection (ATCC, Manassas, VA, #CRL-11233™). Both were cultured according to the ATCC instructions. ReN Cell™ VM (#SCC008) was cultured as per instruction using neural stem cell maintenance medium (#SCM005) and growth factors EGF (GF001) and bFGF (#GF005), all from Millipore Sigma, Burlington, MA.

Differentiation. SH-SY5Y cells were exposed to 30 UM all-trans-Retionic acid (Sigma-Aldrich, St. Louis, MO, #R2625) in serum free cell medium for 10 d with medium change every alternate day. ReNcell VM were differentiated by the removal of growth factors from its culture medium for 10 d.

Hyperphosphorylation. Hyperphosphorylation was induced in SH-SY5Y cells by addition of 30 nM OA (Sigma Aldrich, St. Louis, MO, #459620) in growth medium with 30 µM RA for 24 h. ReNcell VM were hyperphosphorylated using 100 nM QA (SigmaAldrich, St. Louis, MO, #P63204) in culture media for 24 h.

Synthesis of primers and TA DNA library. All primers, Cy5, and amine labelled selected aptamers were purchased from Integrated DNA Technologies (IDT, Coralville, IA). The ssDNA library used in Cell-SELEX contained a central randomized sequence of 30 nucleotides flanked by PCR primer regions to enable the PCR amplification of the sequence 5'-CGCTCGATAGATCGAGCTTCG (SEQ ID NO: 28)-(N)$_{30}$-GTCGATCACGCTCTAGAGCACTG-3' (SEQ ID NO: 29). The chemically synthesized DNA library was converted to a phosphorothioate modified library by PCR amplification using, dATP (aS), resulting in the DNA sequences where the 3' phosphate of each residue is substituted with monothiophosphate groups. The reverse primer was labeled with biotin to separate the sense strand from the antisense strand by streptavidin-coated sepharose beads (PureBiotech, Middlesex, NJ, #MSTR0510) for the next selection round. The concentration of the TA library was determined with a NanoDrop™ 2000 by measuring the UV absorbance at 260 nm.

Cell-SELEX. The initial ssDNA library of 150 pmole was dissolved in binding buffer with a total volume of 350 µl. It was denatured by heating at 95° C. for 5 min and renatured by rapid cooling on ice for 10 min. The treated SH-SY5Y cells at approximately 90% confluence in a 100-mm culture plate were washed twice with washing buffer and followed by incubating with the ssDNA library of 150 pmole for 2 h at 4° C. Following the incubation, for positive selections, the supernatant was discarded, and cells were washed three times with washing buffer to remove any unbound sequences. Cells were scraped off and transferred to nuclease-free water, following another 3× nuclease-free water washes. Cells in nuclease-free water were centrifuged at 300×g for 5 min. QIAamp DNA Mini and Blood Mini kit (Qiagen, Germantown, MD, #51104) were introduced to elute cell membrane fraction. The cell membrane fraction was PCR-amplified to monitor the presence of cell binding efficacy at each cycle. For negative selections, the supernatant was simply pipetted out of the flask and processed for the next cycle of selection. The desired compartment was amplified by PCR and used to prepare the TA for the next round of selection. Two different negative selections were involved. One was differentiated treatment only SH-SY5Y cells at cycles #12 and #13. Another was hepatocyte THLE-3 cells at cycles #20 and #21. A total of 26 cycles of Cell-SELEX were conducted, including two different types of negative selections mentioned above.

Next-Generation Sequencing (NGS). At the studied cycles, the membrane fractions were isolated, and the recovered TA sequences were amplified by PCR. Equimolar quantities of the recovered TA sequences over the range were pooled together and sequenced by Next-Gen DNA sequencing using Ion318 chip (ThermoFisher, Waltham, MA). A four base sequence was introduced during PCR amplification to serve as unique "barcode" to distinguish between the studied cycles. Sequencing results were analyzed by the Aptalinger that uses the markov model probability theory to find the optimal alignment of the sequences.

Aptamer binding studies. Aptamer binding studies were conducted with undifferentiated, differentiated, and hyperphosphorylated SH SY5Y and ReN cell VM grown in 96-wells seeded at 10000 per well. $Kd_{app}$ was measured by the equation $Y=Bmax \, X/(Kd+X)$, with GraphPad Prism 9, San Diego, CA, with a saturation binding experiment; cells were incubated with varying concentrations of Cy5-labeled aptamer in a 100 µl volume of binding buffer containing cells, incubated for 30 min, washed twice, resuspended in 100 µl buffer, and analyzed by a Molecular probes microplate reader equipped with the appropriate excitation and emission filters. All data points were collected in triplicate.

Immunocytochemistry. An eight-well glass plate was coated with a solution of 100 µg/ml Collagen Type I (Thermofisher Scientific, Waltham, MA, #A1064401) dissolved in 0.01N HCl and air dried, PBS washed, and air dried again prior to seeding with 20,000 SH-SY5Y cells per well. Aptamer staining at 100 nM was performed with live cells for 2 h at 4° C. in binding buffer and washed twice with washing buffer. Cells were fixed by incubation for 15 min in 4% formaldehyde in PBS at rt. Non-specific binding was blocked with blocking buffer (G-Biosciences, St. Louis, MO, #786195) for 1 h, and overnight incubation at 4° C. with the rabbit pTau primary antibody (1:100) (Santa Cruz Biotechnology, #: sc-101815) was followed by washing with PBS, and 1 h incubation with goat anti-rabbit IgG secondary antibody, Alexa Fluor 488 (Invitrogen, Carlsbad, CA, #A-11008) for 1 h at rt. Cytoskeletal actin filaments were stained with Alexa Fluor 594 Phalloidin (Invitrogen, #A12381). The cells were covered with VECTASHIELD hardset mounting medium with DAPI (Vector Laboratories, Burlingame, CA, #H-1500) for 5 min at rt. Images were visualized under Olympus Fluoview FV1000 confocal microscopy.

ADx-002 nanoparticle synthesis. L-α-phosphatidylcholine, hydrogenated (Hydro Soy PC; HSPC) and Cholesterol were purchased from Lipoid Inc., Newark NJ, USA. 1,2-distearoyl-sn-glycero-3-phosphoethanolamine-N-[methoxy (polyethylene glycol)-2000] (DSPE-mPEG2000) was purchased from Corden Pharma, Liestahl, Switzerland. DSPE-PEG3400-COOH and Gd-DOTA-DSPE were synthesized in house, lis-rhodamine-DHPE from ThermoFisher Scientific. HSPC, Cholesterol, DSPE-PEG3400-COOH, DSPE-mPEG2000, Gd-DOTA-DSPE, lis-rhodamine-DHPE at molar proportions 31.4:40:0.5:3:25:0.1 were dissolved in ethanol to achieve a total concentration of 100 mM. For the non-targeted control stealth liposomes, carboxy terminated PEG was not included in the lipid mixture. The ethanolic solution of lipids was hydrated with 150 mM saline solution at 65° C. for 30 min, allowing multilamellar liposomes to form. The mixture was then extruded in a 10 ml Lipex extruder (Northern Lipids Inc., Burnaby, Canada) using a 400 nm polycarbonate track-etch polycarbonate filter (3 passes) followed by a 200 nm (3 passes) and finally 100 nM filters. The suspension was diafiltered using a MicroKros cross-flow diafiltration cartridge (500 kDa cutoff) from Repligen, Rancho Dominguez, CA, exchanging the external buffer for phosphate buffered saline (PBS, pH 7.2) for 15 volume exchanges. To form the aptamer conjugated liposomes, liposomes with lipid-PEG-COOH were reacted with amine terminated aptamers using carbodiimide chemistry. The carboxyl groups on the liposomes were activated with 5 mM EDC and 10 mM sulfo-NHS at pH~6 for 5-10 min. The activated liposomes were then immediately reacted with the amine terminated aptamers, and the pH was raised to ~7.3-7.6 by titrating μl amounts of 5 N NaOH. The final concentration of aptamers used in reaction is ~140 μM. The reaction was mixed at rt for 1 h following which the reaction was carried out at 4° C. overnight. The liposomes were dialyzed against PBS to remove unconjugated aptamers using a 300 kDa dialysis membrane. The dialysate (external phase) was concentrated using 10 kD centrifugal separator and washed with PBS to remove residual EDC/s-NHS. The concentrated dialysate was analyzed by NanoDrop Spectrophotometer (ThermoFisher Sci., Waltham, MA, USA) to determine unconjugated aptamer fraction and estimate aptamer density per nanoparticle in ADx-002 formulations. Inductively coupled plasma atomic emission spectroscopy (ICP-AES) was used to measure Gd and phosphorus concentrations of ADx-002 formulations. The hydrodynamic diameter of liposomal nanoparticles in ADx-002 formulations was determined using a dynamic light scattering instrument.

Withaferin A nanoparticle (WNP) synthesis. The allylic alcohol of Withaferin A was selectively activated by exposure to 4-nitrophenyl chloroformate (1.1 eq) at 0° C. for 8 h to give intermediate compound in excellent yield. This was then reacted with DSPE-PEG-NH2-3400 at rt for 24 h. The crude product was dialyzed against water for 2 days and freeze dried to yield DSPE-PEG-3400-Withaferin A. Structures of the intermediate and final products were confirmed by NMR and MALDI. Liposomal nanoparticles containing Withaferin A on its surface were generated by using the ADx-002 composition, substituting the carboxy PEG with the synthesized DSPE-PEG3400-Withaferin A to yield WNP (FIG. 4B).

Mice. All of the procedures were performed with approval from Institutional Animal Care and Use Committee (IACUC) of Baylor College of Medicine. Mice were kept under a 12 h light/dark cycle, with food and water available ad libitum. PS19 mice from Jackson Laboratories (Bar Harbor, ME) B6; C3-Tg (Prnp-MAPT*P301S) PS19Vle/J Stock No: 008169 were used, and experiments were conducted at 2 months of age. The Tg mice develop neurofibrillary tangles by 5 months of age. Age-matched non-transgenic WT mice were used as controls. APP/PS1 mice from Jackson Laboratories B6.Cg-Tg (APPswe,PSEN1dE9) 85Dbo/Mmjax MMRRC Stock No: 34832-JAX were also used for experiements with WNP. These mice generate amyloid plaques by 6 weeks in cortex and 2-4 months in hippocampus without any reported mature tau tangles, but the presence of hyperphosphorylated tau neuritic processes has been observed around plaques.

Magnetic Resonance Imaging (MRI). MRI was performed on a 1 T permanent magnet scanner (M7, Aspect Imaging, Shoham, Israel). Mice underwent pre-contrast baseline scans. Thereafter, mice were intravenously administered one of three nanoparticle MR contrast agents (Tau_1 (SEQ ID NO: 5; DONGYBM), Tau_3 (SEQ ID NO: 6; MUSQD), or non-targeted control liposomes) via tail vein at a dose of 0.15 mmol Gd/kg of body weight. Delayed post-contrast MRI was performed 4 days after contrast agent injections. Pre-contrast and delayed post-contrast MR images were acquired using a T1w-SE sequence and an FSE-IR sequence with the following parameters: SE parameters: TR=600 ms, TE=11.5 ms, slice thickness=1.2 mm, matrix=192×192, FOV=30 mm, slices=16, NEX=4; FSE-IR parameters: TR=13500 ms, TE=80 ms, TI=2000 ms, slice thickness=2.4 mm, matrix=192× 192, FOV=30 mm, slices=6, NEX=6. Coil calibration, RF calibration, and shimming were performed at the beginning of study for each subject. The pre-contrast scans provide a baseline for calculation of signal enhancement from resulting post-contrast scans. Two-standard deviations above the mean variation within WT control animals was used as the cutoff signal intensity for identifying tau positive animals. Six Tg mice and six WT mice were used for testing of each nanoparticle contrast agent formulation. ROC curves were generated on a six point ordinal scale by plotting the TPF against the FPF based on imaging-based identification of tau-positive animals using the cutoff signal intensity and comparing against histological confirmation of tau pathology as a gold standard. A fitted curve was generated against the empirical points plotted on the graphs. Qualitative and quantitative analysis of MRI images was performed in OsiriX (version 5.8.5, 64-bit, Pixmeo SARL, Geneva, Switzerland) and MATLAB (version 2015a, Math Works, Natick, MA).

Immunohistochemistry. After the final MRI scan, the mice were euthanized and perfused extensively with 0.9% saline followed by 4% paraformaldehyde for 15 min. The brains were then immersion-fixed in 4% formaldehyde for 48 h at 4° C., transferred to 30% sucrose for cryoprotection, and embedded in OCT. Phenotypic confirmation for the presence of phosphorylated tau and VIM was performed on 25 μm thick brain sections. Antigen retrieval in pH=8.5 citrate buffer was executed in a 1200W GE microwave for 15 min. After 15 min of cooling, 25 μL of 1:50 dilution of primary p-tau antibody, namely either AT8, AT100, or AT180, which recognize different p-tau species, were incubated in a tray (RPI, Mt. Prospect, IL #248270) designed for microwave enhanced immunostaining procedures for 3 min at power level 3. After a 2 min cooling, sections were washed with PBS and incubated for 3 min with a 1:100 dilution of appropriate secondary antibody. DAPI staining proceeded after 2 min of cooling and a PBS washing. ProGold Antifade (Invitrogen, Carlsbad, CA, #P36030) was used to mount slides, which were visualized on Olympus Fluoview LV100. Scanning of whole sections was also conducted using a Biotek Cytation 5 slide scanning microscope. Antibodies—AT8 (#MN1020) and Vimentin SP20 (#MA516409) were purchased from Thermo Fisher Scientific, Waltham, MA, Vimentin D21H3 from Cell Signaling Technology, Beverly, MA, #5741 T, and cell-surface vimentin from Abnova, Taipei City, Taiwan, #H00007431-M08J.

Target Identification. The protein targets of Tau_1 (SEQ ID NO: 5; DONGYBM), Tau_3 (SEQ ID NO: 6; MUSQD), Tau-4, and Tau-5 were identified by affinity-pull down using the selected aptamers as the capturing reagent followed by mass-spectroscopy. A scrambled DNA sequence, R2, was used as a control. The hyperphosphorylated SH-SY5Y cells, at 90-95% confluence, were washed with cold PBS buffer and incubated with biotinylated selected aptamers with 25 mmol/l each at 4° C. in PBS, respectively. After 2 hours of gentle agitation, SH-SY5Y cells were cross-linked with 1% formaldehyde for 10 min at rt. The formaldehyde crosslinking was quenched with glycine. Cells were scraped from the plate, washed, lysed with lysing buffer (Thermofisher Scientific, #87787), and treated with protease inhibitor mixture. The lysates were freeze-thawed for 30 min on ice and cleared by centrifuging at 10,000×g for 2 min at 4° C. To pull down the cross-linked proteins, equal amounts of cell lysate were incubated with prewashed streptavidin magnetic beads for 1 h at rt with continuous rotation. Protein digestions were performed on the beads to isolate targeted proteins and processed for mass spectrometric analysis. Each sample was analyzed in triplicate. The raw data files were processed to generate a Mascot Generic Format with Mascot Distiller and searched against the SwissProt_2012_01 (Human) database using the licensed Mascot search engine v2.3.02 (Matrix Science, Boston, MA) run on an in-house server.

The ATN research framework suggests the need for biomarkers to diagnose and classify AD. Under this framework, CSF based detection of Aβ and tau (total, and phosphorylated) have been reported but only at the prodromal stage of disease, in patients with mild cognitive impairment. Non-invasive neuroimaging tools, such as structural MRI, to diagnose and monitor neurodegeneration, show a definitive correlation with cognitive decline, visualizing atrophic regions that depict neuronal injury in late stage disease. However, a reliable marker of early stage disease in the presymptomatic stage is yet to be described.

While the role of Aβ and tau in the development of AD, and the mechanism of transition from presymptomatic to symptomatic AD are yet unclear, the time scale of the transition is generally accepted to be over a period of 10-20 years. Aβ deposits are considered the start of neurodegeneration, but recent studies indicate that tau pathology shows a stronger correlation with disease progression suggesting that the limitation of current tests is their inability to identify early stage pathological tau. CSF presence of hyperphosphorylated tau species p-181 and p-217 is associated with Aβ deposition that precedes a positive tau PET but only has a concordance of 50%-70%. Taken as a whole, the roles of Aβ and tau deposition in disease progression, and the role of Aβ in the spread of initial tau aggregates, strongly suggest that a biomarker of pathological tau at a presymptomatic stage of the disease is likely to advance detection by several years and constitutes the motivation for this work.

Initial tau aggregation is thought to be triggered by an imbalance in cellular homeostasis caused by dysregulated phosphorylation. Several kinases can phosphorylate tau, theoretically at 85 different positions of which at least 45 have been observed experimentally. Combined with reduced phosphatase activities in AD, the altered kinase-phosphatase balance yields hyperphosphorylative conditions that cause abnormal hyperphosphorylation of tau. Disruption of the normal function of tau, modulating microtubule dynamics by lowering its binding capabilities, increases the level of cytosolic free tau leading to aggregation and fibrillization of tau that spreads throughout the connected brain, seeding the pathology. This initial process of hyperphosphorylation may be associated with changes on the surface of hyperphosphorylative cells. Through the instant work, these surrogate markers of tau hyperphosphorylation that presage future tau pathology have been identified.

Using SH-SY5Y cells as a model of neuronal hyperphosphorylation, an RPPA analysis was used to demonstrate elevated levels of surface molecules specific to the hyperphosphorylative state. Cell-SELEX capturing the differences between the surface of hyperphosphorylative cells and normal cells allowed the selection of phosphorothioate modified short DNA aptamers that bound with high affinity and specificity to hyperphosphorylative cells (FIG. 2A). Having identified unique aptamers that bound such markers, MR molecular imaging contrast agents were developed that recognize the surface of cells in hyperphosphorylative state. SH-SY5Y cells are not true neurons, but rather, a cell line originating in a neuroblastoma, a tumor of embryological neural crest origin. However, they can be induced to differentiate to a neuronal phenotype (as in the current work). While primary neuronal culture or immortalized neuronal cells, e.g., ReN-VM, may offer alternative models of neurons, the aptamer hits from the SELEX screen have been functionally tested in a Tg mouse model of tau deposition. Their performance has been validated, supporting the position that the choice of cell model was adequate to identify suitable markers of tau hyperphosphorylation.

The possible binding targets of the aptamers have been narrowed down, and the data suggest that cell surface VM is a likely target. The specific presence of cell surface VIM on the surface of SH-SY5Y cells in a hyperphosphorylative state and on P301S mouse brain sections has been confirmed. VIM is an intermediate filament protein that undergoes constant assembly and/or remodeling and is usually associated with mesenchymal cells. The assembly state of filaments is linked to their phosphorylation state; phosphorylation promotes disassembly. VIM contains more than 35 phosphorylation sites targeted by multiple kinases and phosphatases, allowing it to adjust IF dynamics dependent on its environment. Mechanical, chemical (toxins, hypoxia), and microbial stresses upregulate VIM, and its phosphorylation allow cells to adjust their mechanical properties. The balance of different oligomeric forms influence dynamic cell processes including adhesion, migration, and invasion, including stress-induced signaling. Vim IFs (~10 nm) distributed throughout the cell by association with microtubules (tubulin, 24 nm) regulating cell-migration, and microfilaments (actin, 7 nm) regulating cell-contractility, form the cytoskeletal network and provide mechanical support for the plasma membrane where it contacts other cells or the extracellular matrix. During the biological process, epithelial to mesenchymal transition, wherein non-motile, polar epithelial cells transform to motile invasive non-polar mesenchymal cells, cells also undergo a cytoskeletal reorganization that includes changes in cell-membrane integrity, disassembly of junction proteins, increased stress-fiber formations, and altered cell-surface protein expression. Changes in the localization of proteins is a hallmark of this pathologic process. The observation that VIM is upregulated and translocated to the cell surface in the early stages of tau hyperphosphorylation suggests a possible role for EMT-related processes at the start of a slow progression towards AD pathology.

PET is the leading modality for clinical molecular imaging, driven by its high contrast sensitivity; however, it suffers from poor spatial resolution on the order of 5-10 mm, high cost, limited access to radioactive tracers, and radiation exposure. Nanoparticle-enhanced MR imaging overcomes all these obstacles, but historically has not achieved high enough sensitivity. Liposomal nanoparticles have been demonstrated exhibiting large numbers of Gd chelates in the external bilayer leaflet, with hyper-T1 relaxive properties resulting in contrast sensitivity that rivals nuclear imaging.

An often-quoted concern about the use of nanoparticles for brain imaging centers on whether these particles can penetrate the blood-brain barrier (BBB). The notion of the BBB arose primarily in the context of delivery of relatively large amounts of therapeutic molecules to brain tumors. For imaging, however, relatively small amounts of contrast agent need to be delivered. Further, the convective and diffusive transport of molecular and particulate species through the porous choroid plexus is well known. The transport of liposomal nanoparticles into the CSF via this route has been demonstrated. A liposomal MRI agent targeting amyloid plaque that successfully traverses the BBB following intravenous injection and binds plaques, enabling accurate imaging of amyloid pathology by T1-weighted MRI has been demonstrated.

In P301S mice, the earliest reported histopathological studies are at the age of 2.5 months and report no tau pathology. "Tau seeding" the cell-cell transfer of pathogenic tau aggregates has been reported using brain homogenates at 1.5 month of age. Therefore, P301S mice at 2 month of age were chosen for these studies, an age at which tau seeding should be taking place, but frank tau pathology should be absent. The mice were injected with ADx-002 nanoparticles targeted either by the Tau_1 (SEQ ID NO: 5; DONGYBM) aptamer or the Tau_3 (SEQ ID NO: 6; MUSQD) aptamer. When imaged by T1-weighted MRI sequences, designed to optimize signal from the Gd chelate induced T1 relaxation caused by the liposomal-Gd nanoparticles, signal enhancement was observed in the cortex and hippocampus regions of the brain. Hyperphosphorylative conditions were confirmed by post-mortem IF staining with AT8 antibody that recognizes the S202 and T305 pTau species. Signal enhancement was not observed in non-Tg mice or in Tg mice injected with untargeted nanoparticles, supporting the specificity of Tau_1 (SEQ ID NO: 5; DONGYBM) and Tau_3 (SEQ ID NO: 6; MUSQD)-bearing nanoparticle binding to target.

Figure 10:
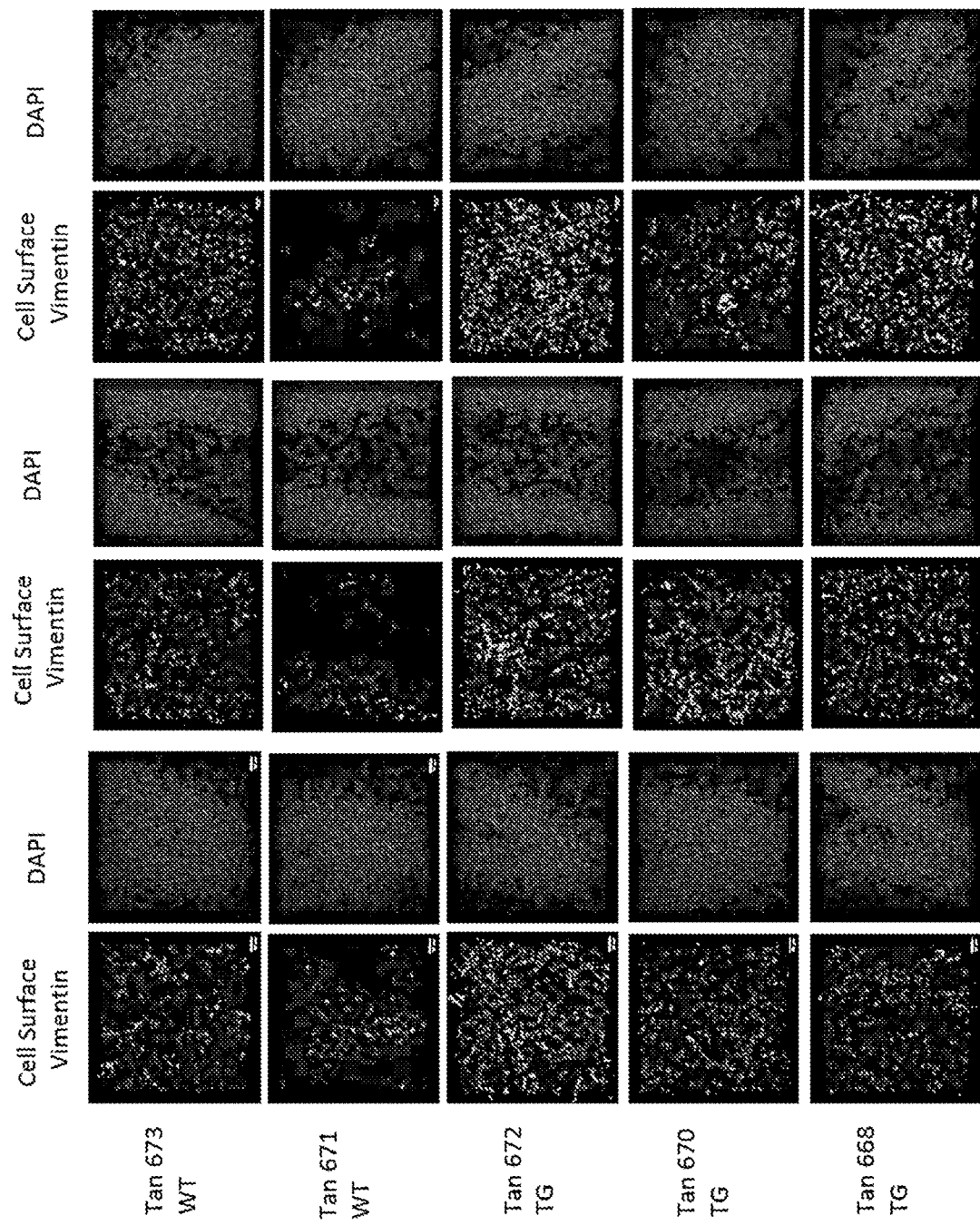
FIG. 10 shows cell surface VIN expression on 2 month old P301S mice. The mice were perfused with heparin/PBS and formalin, and brains were isolated and processed to immunolabel frozen sections with cell-surface VIM antibody (clone 84-1, Abnova) that specifically stains VIM translocated to the cell surface. Tg mice showed a higher expression in comparison with WT mice.

Validation is herein provided of VIM binding ADx-002 nanoparticles by the use of a small molecule, Withaferin A, known to bind VIM at its highly conserved cysteine residue in coiled-coil 2B domain. Intraveneously injected WPNs exhibited binding in the same brain regions as ADx-002 and maintained specificity and sensitivity to the phosphorylative state, with signal enhancement observed only in Tg mice and not in WT mice. Additionally, similar results are shown in another mice model (APP/PSEN1). Taken together, this in vivo data further supports the use of such particles as detectors of hyperphosphorylation that leads to the initiation of tau pathology in AD. The higher expression of CSV was confirmed in transgenic P301S mice at 2 months of age by immunofluorescence (FIG. 10).

While PET is the mainstay of molecular imaging and exhibits remarkable sensitivity, there are several limitations posed by this methodology. Access to PET imaging is limited, even in the relatively well-served U.S., and is skewed toward high density urban centers. PET costs are very high due to the need for same day radiosynthesis and rapid decay of the isotopes. Longer half-life isotopes cause higher radiation exposure. This tradeoff between half-life and radiation exposure greatly limits the reach of PET to a wider patient population. Current PET tau tracers recognize the tau β-sheets in the PHF and NFT present in tauopathies. This conformation is not unique to tau, and the in vivo specificity is circumspect, limiting its interpretation. Off-target binding of Flortaucipir, an approved tau PET agent, has been reported since it binds the MAO-B enzyme in the brain. Further, the vast majority of pathological tau is intracellular, posing a significant barrier to PET tracers that must navigate to the site of tau pathology, bind the target, and have all unbound tracer molecules cleared from the brain before the radioactive signal decays. The choice of MRI as the detection modality is based on hyper-T1 relaxive properties of nanoparticles with surface conjugated Gd chelates, bringing detection sensitivity to the same range as nuclear imaging, and the MRI agent does not suffer from the rapid signal decay of PET agents, allowing plenty of time for unbound tracer to clear from the brain before imaging. The choice of a cell surface surrogate marker of tau hyperphosphorylation avoids the need to bind an intracellular target. Finally, MRI imaging is already included in AD management and can be adjusted with agents such as ADx-002 nanoparticles to constitute a highly sensitive and specific test for future tau pathology.

What is claimed is:

1. A method for imagining tau pathology in a subject, the method comprising:
administering to the subject a detectably effective amount of a targeting ligand-liposome conjugate comprising a targeting ligand represented by Compound I:

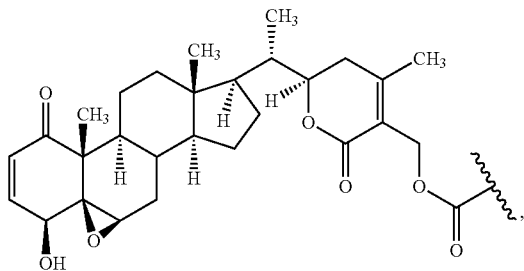

wherein the targeting ligand specifically binds to a cell surface marker of tau pathology, and
wherein the targeting ligand is linked to a liposome comprising an imaging agent, and
imaging at least a portion of the subject to determine if that portion of the subject exhibits tau pathology.

2. The method of claim 1, wherein the cell surface marker of tau pathology comprises a cell surface marker of tau hyperphosphorylation.

3. The method of claim 1, wherein the cell surface marker of tau pathology comprises the protein vimentin.

4. The method of claim 1, wherein the imaging agent comprises a magnetic resonance imaging (MRI) contrast enhancing agent.

5. The method of claim 1, wherein the liposome comprises a membrane, the membrane comprising:
a first phospholipid;
a sterically bulky excipient that is capable of stabilizing the liposome;
a second phospholipid that is derivatized with a first polymer;
a third phospholipid that is derivatized with a second polymer, the second polymer being conjugated to the targeting ligand; and
the imaging agent, which is encapsulated by or bound to the membrane.

6. The method of claim 5, wherein:
the first phospholipid comprises HSPC;
the sterically bulky excipient that is capable of stabilizing the liposome comprises cholesterol;
the second phospholipid that is derivatized with a first polymer comprises DSPE-PEG;
the third phospholipid that is derivatized with a second polymer, the second polymer being conjugated to the targeting ligand comprises DSPE-PEG conjugated to Compound I; and
the imaging agent comprises DSPE-DOTA-Gd.

7. The method of claim 5, wherein:
the first phospholipid comprises HSPC;
the sterically bulky excipient that is capable of stabilizing the liposome comprises cholesterol;
the second phospholipid that is derivatized with a first polymer comprises DSPE-PEG2000;
the third phospholipid that is derivatized with a second polymer, the second polymer being conjugated to the targeting ligand comprises DSPE-PEG3400 conjugated to Compound I; and
the imaging agent, which is encapsulated by or bound to the membrane comprises DSPE-DOTA-Gd.

8. The method of claim 5, including about 600 molecules of conjugated Compound I.

9. The method of claim 5, wherein the third phospholipid that is derivatized with a second polymer, the second polymer being conjugated to the targeting ligand, comprises:

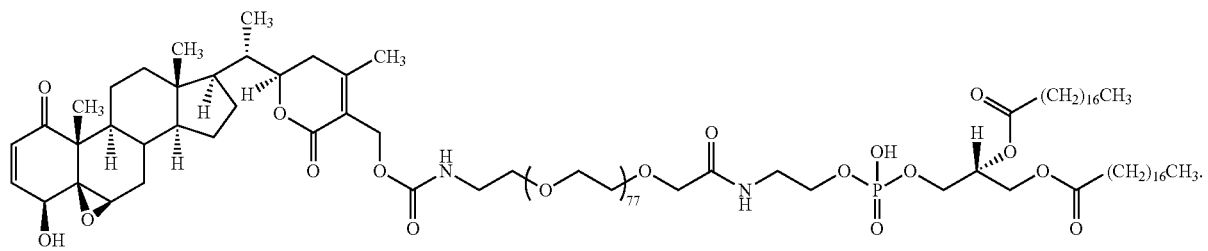

10. The method of claim 1, wherein the portion of the subject includes a portion of the subject's brain.

11. The method of claim 1, wherein the imaging indicates a level of tau pathology sufficient to diagnose the subject as having early stage AD.

12. The method of claim 1, wherein the imaging agent is an MRI contrast enhancing agent, and the level of binding is determined using MRI.

13. The method of claim 1, wherein the administering to the subject comprises contacting a biological sample obtained from the subject with the targeting ligand-liposome conjugate.

14. The method of claim 13, wherein the liposome further comprises a detectable label, and wherein the method further comprises washing the biological sample to remove unbound targeting ligand liposome conjugate and detecting tau pathology in the biological sample by determining the amount of detectable label remaining in the biological sample.

15. The method of claim 14, wherein the biological sample is a sample containing neural cells.

\* \* \* \* \*